(12) United States Patent
Shin et al.

(10) Patent No.: US 10,034,566 B1
(45) Date of Patent: Jul. 31, 2018

(54) SYSTEM AND METHOD FOR SAFE REMOVAL AND DISPOSAL OF GLOVE

(71) Applicants: Yoon Ki Shin, Ellicott City, MD (US); Young Jun Kim, Nashville, TN (US); Isaac Hyunjoong Shin, Ellicott City, MD (US); Joshua Hyunchan Shin, Ellicott City, MD (US); Jun Young Lee, Ellicott City, MD (US)

(72) Inventors: Yoon Ki Shin, Ellicott City, MD (US); Young Jun Kim, Nashville, TN (US); Isaac Hyunjoong Shin, Ellicott City, MD (US); Joshua Hyunchan Shin, Ellicott City, MD (US); Jun Young Lee, Ellicott City, MD (US)

( * ) Notice: Subject to any disclaimer, the term of this patent is extended or adjusted under 35 U.S.C. 154(b) by 33 days.

(21) Appl. No.: 15/387,653

(22) Filed: Dec. 22, 2016

Related U.S. Application Data

(60) Provisional application No. 62/245,245, filed on Oct. 22, 2015.

(51) Int. Cl.
| | |
|---|---|
| *A47G 25/90* | (2006.01) |
| *A61B 42/00* | (2016.01) |
| *A61B 42/50* | (2016.01) |
| *A61B 50/30* | (2016.01) |

(52) U.S. Cl.
CPC .......... *A47G 25/904* (2013.01); *A47G 25/90* (2013.01); *A61B 42/00* (2016.02); *A61B 42/50* (2016.02); *A61B 50/30* (2016.02)

(58) Field of Classification Search
CPC ...... A47G 25/90; A47G 25/92; A47G 25/904; A61B 42/00; A61B 42/50; A61B 50/30
See application file for complete search history.

(56) References Cited

U.S. PATENT DOCUMENTS

| | | | | |
|---|---|---|---|---|
| 6,021,935 | A * | 2/2000 | Yonezawa | A47G 25/904 223/111 |
| 7,726,526 | B2 * | 6/2010 | Cattenhead | A47G 25/904 223/111 |
| 2007/0170213 | A1 * | 7/2007 | Gaines | A47G 25/904 223/111 |
| 2007/0170214 | A1 * | 7/2007 | Kelly | A47G 25/904 223/111 |

FOREIGN PATENT DOCUMENTS

| | | | |
|---|---|---|---|
| JP | 2001299558 A | * | 10/2001 |
| JP | 2003230570 A | * | 8/2003 |
| JP | 3200844 U | * | 11/2015 |
| JP | 2016180201 A | * | 10/2016 |

* cited by examiner

*Primary Examiner* — Ismael Izaguirre

(57) ABSTRACT

A mechanical system that aids the removal of gloves from hand is provided. The system employs one or more hooks to widen the opening of a glove from or about the hand to aid the glove's removal from the hand. Once a glove is removed, both the glove and the hook(s), or a disposable portion thereof, are safely dropped below into a waste compartment. A plurality of hooks, or disposable portions thereof, are stored and supplied within a mechanical compartment for use as needed. A fresh hook(s) is dispensed when another glove is to be removed from a user's hand. One or both hands of a user may be safely de-gloved and dispensed during one operational sequence.

15 Claims, 16 Drawing Sheets

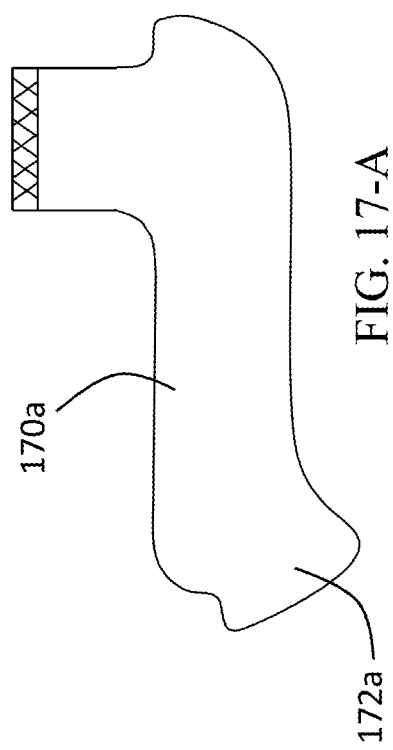
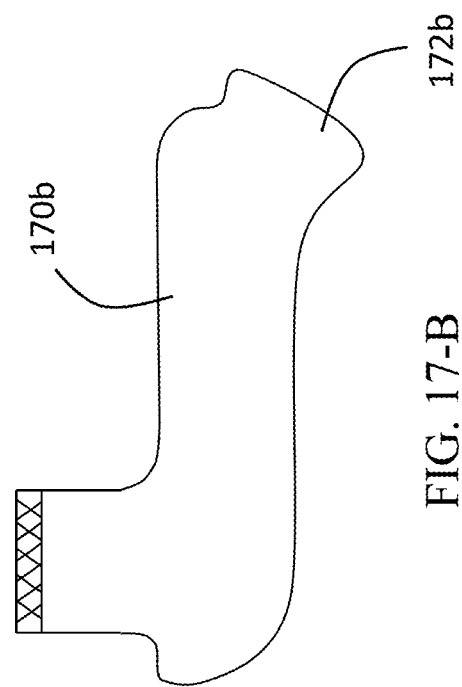
FIG. 17-A
FIG. 17-B

SYSTEM AND METHOD FOR SAFE REMOVAL AND DISPOSAL OF GLOVE

RELATED APPLICATIONS

This Application is based on provisional Patent Application No. 62/245,245, filed Oct. 22, 2015.

BACKGROUND OF THE INVENTION

Protective gloves of numerous types are known in the art for a wide range of different applications. Generally, a protective glove provides an important barrier between the environment and one's skin to reduce the risk of harmful exposure to and transmission of infectious or otherwise hazardous materials. A glove is formed by a layer or multiple layers of material that envelops the hand, the wrist, and a portion or all of one's forearm. The glove is used typically to cover the hand/wrist/forearm parts to provide protection either from or to a given environment of various types, including but not limited to heat, radiation, mechanical, chemical, and or biological. A person wears a glove by inserting his or her hand through the glove opening and removes the glove by taking the hand out of glove, often using his/her other hand. The glove may be made of any material that can either stretch or not stretch. However, the persistence of certain iatrogenic diseases strongly suggests that the barrier typically provided by the glove is not optimal, or at least not optimally preserved through all phases of use. The breach of a glove's barrier can come from the absorption/penetration/infiltration of hazardous material through the glove's material, a tear in the glove, or during the removal of contaminated glove. The present invention addresses these and other shortcomings affecting the use of protective gloves, so as to, among other things, minimize the risk of breaching the glove's barrier during the removal of the gloves. In accordance with certain aspects of the present invention, the disclosed system and method relate to facilitating safe and effective removal of gloves.

SUMMARY OF THE INVENTION

A system and method formed in accordance with certain embodiments of the present invention provide for safe removal of one or more gloves from a wearer's hand(s). The system and method provide for removal of the glove(s) without unduly compromising the wearer's health and safety during the removal process, and preserving the wearer's protection from harmful materials contacted by the glove(s).

These and other objects are attained in a system for safe removal and disposal of a glove from a user's hand. The system includes a mainframe defining a de-gloving compartment. At least one hook base portion is displaceably supported relative to the mainframe. At least one hook member is coupled to the hook base portion, and at least a part of the hook member defines a disposable portion detachable from the hook base portion. The disposable portion of the hook member terminates at an engaging tip configured for insert within the glove worn on the user's hand. The hook base portion is displaceable to selectively position the engaging tip of the hook member into the de-gloving compartment, the glove being removed responsive to relative displacement between the engaging tip and the user's hand upon engagement of the glove worn thereon. The removed glove is released with the disposable portion upon detachment thereof from the hook base portion into a receptacle disposed in communication with the de-gloving compartment, while the hook base portion remains shielded from the de-gloving compartment.

In accordance with certain embodiments, a method is provided for safe removal and disposal of a glove from a user's hand. The method includes establishing a mainframe and defining a de-gloving compartment therein. At least one hook base portion is displaceably supported relative to the mainframe. At least one hook member is displaceably carried on the hook base portion, with at least a part of the hook member defining a disposable portion detachable from the hook base portion. The disposable portion of the hook member terminates at an engaging tip configured for insert within the glove worn on the user's hand. The hook base portion is displaced to selectively position the engaging tip of the hook member into the de-gloving compartment. The glove is removed with the disposable portion of the hook member responsive to relative displacement between the engaging tip and the user's hand upon engagement of the glove worn thereon. The hook base portion is maintained shielded from the de-gloving compartment, whereby the removed glove is safely released with the disposable portion upon detachment thereof from the hook base portion into a receptacle disposed in communication with said de-gloving compartment.

In certain embodiments and applications of the subject system and method, a set of movable hooks are utilized to remove a glove from the wearer's hands without the need for the wearer or other individual to extraneously touch or otherwise manipulate the glove. The hook provides sufficient hold for opening of a throat of the gloves wide enough for the wearer to withdraw his/her hand from the glove without having to hold the glove down or pull the same away. The hooks may be discarded after use to minimize contamination.

DETAILED DESCRIPTION OF THE PREFERRED EMBODIMENTS

Figure 1:
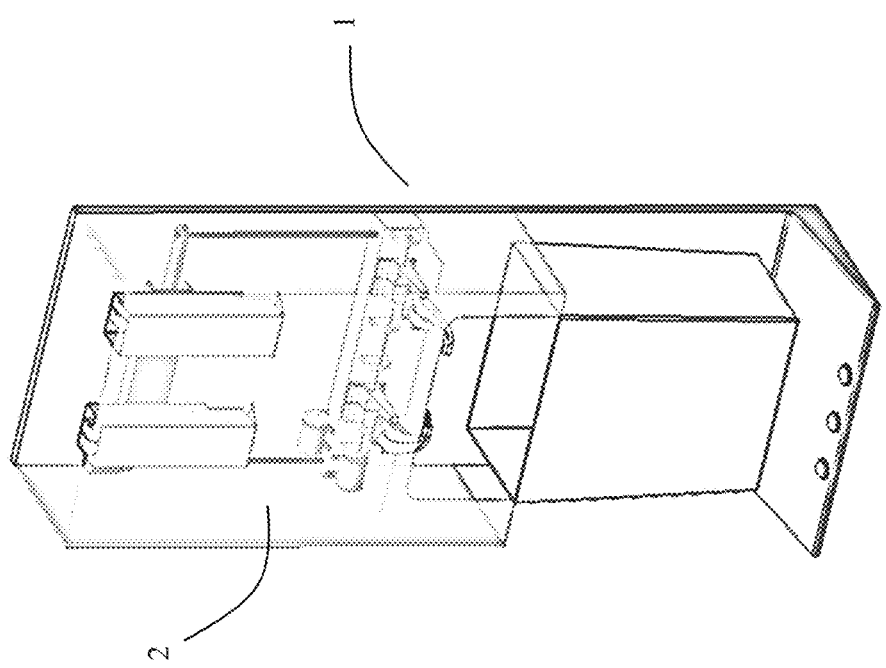
FIG. 1 is an isometric view of system formed in accordance with one exemplary embodiment of the present invention.

The present invention is generally directed to automated measures that help de-glove a user's gloved hand. The disclosed system and method may be used in such applications and settings as a hospital or other healthcare institutions. The automated measures may be employed in various other settings where there is either a danger posed by exposure to noxious materials such as chemical toxins, germs, harmful organisms. Once a protective glove is worn and used, the outer surface of the glove worn is typically soiled and/or contaminated with such toxins, bugs, viruses, parasites, or the like.

Even if the glove may have provided effective protection for the user against harmful contact or contamination during use, the risk of such contact/contamination is heightened when it comes time for the glove's removal. Often, it is in the process of taking off the glove that a user inadvertently makes contacts with what's on the surface of the outside surface of the glove. Currently, in a hospital setting, for example, when a dirty glove is to be removed, it is typically removed by the individual wearing the glove with their own hands. In such settings, this is where the protective barrier is frequently breached/compromised. The action of removing the glove from one hand with the help of the free hand and fingers presents prime opportunities for unwanted contact/contamination.

This may be for instance by direct contact, where the free hand is itself still gloved. When that gloved hand is used to help initiate glove removal from the other hand, the contaminants on the outer surface of the helping free hand's glove may contact the protected skin at or near the hand being de-gloved. Anything other than the utmost care and the most delicate handling may also result in the contaminants from the glove being removed to somehow contact the individual's exposed skin. The problem is exacerbated where the protective glove is formed of a highly elastic material, such as latex or other rubbery composition, which is prone to stretching and elastic snap-return when released. During the process of glove removal, accidental stretching and release may cause some noxious, contaminant material to be projected from the elastic glove as a result, thereby getting aerosolized. This may essentially splatter the user or a bystander, or may splatter to contaminate a nearby instrument. When the instrument is subsequently touched by someone in the room (such as the patient, patient's family, or a caretaker), not only is that individual contaminated, the individual may go on to unwittingly contaminate others thereafter. Indeed, this may pose a serious threat, as it may provide a highly effective mode of transmission for various transmittable biological organisms or chemical materials having the potential to cause grave harm.

In accordance with certain aspects of the present invention, the disclosed de-gloving system permits an individual who's wearing soiled gloves to inserts their hands into a substantially enclosed space, to enable the system to then automatically engage and remove the gloves from the individual's hands. Whatever is on the outside surface of a glove gets removed and discarded with the used glove into a waste compartment or receptacle. The material that comes in contact with the glove is thereby contained, and remains substantially isolated from the individual and from surrounding areas. The contaminant-borne glove is preferably deposited immediately upon removal from the individual's hand into a biodegradable container, or a waste bag/sheath that may be processed accordingly, if in a hospital.

Such a de-gloving system would be of great use particularly in or about an operating room, where surgical gloves worn by surgeons, nurses, and other personnel are used not just as a barrier against simple skin-skin contact, but serve to shield the personnel from exposure to actual blood. Typically, much blood contacts and remains on a surgical glove—blood which may contain transmittable organisms like HIV, Hepatitis C, or the like. Many precautions are taken in the operating room, but even with the most advanced technologies available in the operating room—used gloves are still normally removed manually, often with the help of other individuals who are needlessly exposed to potential contamination thereby, otherwise by the individual wearing the glove him/herself. As noted, this poses real risks of transmitting what's on the outer surface of the worn/spent glove to both the individual wearing the glove as well as to another individual assisting in the glove's removal.

Again, there are several notable hazards the system generally protects against. It protects against contamination of the individual who's actually wearing as they remove the glove, as one will invariably get something—some of one's skin touching the noxious contaminant on the outside of the glove. In addition, since the gloves are often made of elastic material composition, there is a real tendency to inadvertently flick, or fling, if you will, to accidentally propel the material from the glove to the surrounding areas.

There is no system or method heretofore known which adequately addresses these and other risks of accidental exposure and/or contamination of individuals or surrounding areas during the process of effective glove removal.

In terms of safety procedures or best practices to guard against such harmful exposure or contamination, there are but unregimented quasi-protocols where, say, the surgeon needs a blood contaminated glove removed. Often, a circulating nurse or an assistant nurse comes in and with their own gloved hand, removes the glove. This is often done out in the open. Even if the assistant were adequately protected, there remains the chance of hazardous material from the glove's surface splattering during removal, given a surgical glove's typically elastic, rubberized material composition. Noxious organisms and materials (collectively referred to herein as 'materials') like bugs, bacterium, viruses, toxins may be released into the surrounding environment, even in such health-conscious settings as hospitals and medical centers. There is no known system—mechanized or otherwise—to correct this.

Extraneous protective measures such as over-the-shirt sleeve extensions are known to be used to protect against liquid material splattering, where potential contamination all the way up to the elbows (or beyond) is expected. But there remains the need to protect against accidental exposure during removal of the glove and extension removal.

Going beyond the operating room setting, in other settings such as when a healthcare provider is seeing patients bedside or at a clinic, there remains an ongoing challenge to minimize the risk of harmful biological transmission, since the healthcare provider unavoidably comes into contact both with patients and various items in their rooms. They shake hands and touch patients' bodies to examine. Yet in those scenarios, there are no measures known for automatically assisting one to de-glove.

Measures may of course be taken after the fact to remedy accidental exposure during glove removal. For example, if an individual in the process of taking a glove off gets some contaminant on one's self. The individual may then take decontamination measures, scrubbing afterwards, washing their hands, and so on. But contamination in itself in some cases may be sufficiently grievous, and not readily remedied after the fact. In the case of E-bola or other such particularly noxious threats, for instance, it is essential to altogether avoid exposure in the first place.

A history of experience shows an ongoing need for preventive measures against contaminant transmission, even with heightened social awareness and widespread good practices. Take for instance the culture of 'washing your hands.' That's been driven home effectively in most places throughout the modern world. Yet, various oxygenic diseases continue to get passed by patients to healthcare providers; healthcare providers to patients, and patients to patients, etc.

So there's pressing ongoing need to preserve the protective barrier as much as we can—particularly in these sorts of scenarios where any transmission may not necessarily be anticipated. That's where the threat may be particularly troublesome, because if someone comes in relatively healthy, there may be little worry about them transmitting any bug to all. In those sorts of scenarios, a caregiver's guard comes down. The disclosed system and method help to effectively preserve a protective barrier. The subject de-gloving system and method serves generally to maximize and extend a glove's protective barrier from periods of use to its removal and discarding.

Regarding a glove de-gloving rack, or even something as simple as just a hook or shoehorn-type engaging structure within perhaps a bin, one may place his/her hands into the bin and engage the hook structure then manipulate the hands and arms to remove the hands from out of the gloves. For example, by manipulating the hands to let the hook structure clip onto the mouth of a glove about a wrist, one might just work the glove off the hand. The hook structure would essentially substitute for an assistant's finger. But that process would be vulnerable to factors like accidental splattering.

Another concern is that the hook, or shoehorn-type, structure itself, could become the carrier because once it is used. It could contaminate an individual making subsequent use of it, unless it is replaced or sterilized effectively beforehand.

Preferably, anything that comes in contact with the glove should be disposable. That's important for various reasons. Among other things, if you look at most medical devices that are being used in the hospital, that is what they have asked for unless it is a really expensive material that require exhausted cleaning to be used after surgery or applications on patients. Where possible, any supplies and equipment, hospitals typically want to actually make disposable. Where possible, it is preferable to make items used during an operation to be disposable, much like a glove is disposable after use in a biodegradable container. Similarly, items that come in contact with a soiled glove should be contained in a container and housed in a biodegradable material to be disposed of appropriately.

It is not desirable to have assistants helping to de-glove, even with their own hands protectively gloved, since that person must at some point also remove their glove at some point. That may just amount to transferring the risk. With each transfer, the potency of risk may get lower, but at some point, somebody has to actually use their own bare hands to de-glove with such human-assisted de-gloving.

A system disclosed in connection with certain embodiments of the present invention includes one or more hook members used for engaging and moving portions of the glove, which hook members are preferably formed with one or more air tips from which, preferably, a puff or a stream of air may be released. The tips then serve to blow air to separate the glove material from the wearer's skin and create a virtual potential space.

Once the tips of the hook members go in between the glove material and skin, air blows therefrom. The hook members are moved apart to widen the mouth opening at the base of the glove, so that the user's hand may be pulled out more easily. A human hand tends to be round at the base, but from the palms to the finger tips it tends to be somewhat flat. Therefore, with hook members stretching the glove's opening sideways, then it's easier for the hand to be withdrawn from the glove.

As a result, the meaty part of your hand may easily fit through the widened glove mouth opening without causing the slingshot effect. The thumb part of the hand is the ulmer. The back part is the dorsum. The front part is the palmer.

Briefly, there are a number of objects realized by a system and method provided in accordance with certain aspects of the present invention. One is that manual intervention obviated. At least the primary operations are mechanically and automatically driven. A barrier is maintained between the wearer and the removal compartment/chamber and disposal container. Any kind of splattering that might occur is contained within this chamber. So there is provided an effective way to grab a hold of the glove and remove it, preferably with a supplemental feature like air blowing or stretching to open the mouth of the glove, such that a user's hand comes out with minimal stretching and sling-shotting of material. Even within the confines of the compartment, there is some opening, and the chance of anything coming out of that opening should be minimized.

Once de-gloving is done, everything just drops down to the disposal container, preferably by gravity assist. So once it goes into the container—and the container is already pre-lined with a suitable liner bag—a filled bag may be taken out and disposed of accordingly.

While the system and method disclosed herein may be illustratively described in connection with a hospital or other healthcare applications, they may be used in other suitable applications. For example, in a chemical lab—to avoid undue exposure to, say, a carcinogenic material being worked with in the lab, the subject self-operated system may serve to contain and safeguard the glove-removal process, so that it occurs safely and effectively, and in a manner that avoids splattering.

The system and method may be used in hazardous material cleanup or handling applications. They may be used as well in food producing for manufacturing or restaurant areas, where they use many gloved hands for many reasons. There may be some differences in how one prepares the container to make sure it is a "medical device" as opposed to some other . . . but the general idea is that the system and method may be adapted for in other areas. Individual handling food—they have gloved-handling of food—if they have a very small device in the corner after they're done, they use the de-glover device/system instead of using their own fingers to remove a soiled glove.

Because in those scenarios, they're not worried about transmission, they're worried about just cleanliness of their hand, this may be reasonable. One can imagine numerous other work environments for use of the disclosed system and method. Say one is in an area where one uses lots of oil or material that is harmful enough to guard against skin contact. When a glove gets covered with this, the system and method may be suitably employed in a mechanic shop or the like. The stakes in terms of threat to health maybe a little bit lower than in a medical device/system, but the potential harm due to direct exposure to skin may nonetheless necessitate stringent barrier requirements and their effective preservation.

It's not just a toxin that you have in medical settings; you have infectious living organisms that move, migrate, and adapt. Whereas in working environments like restaurants, the need to create an extremely rigid, stringent barrier may not be as strong, similar technology could be used in those facilities as well.

In restaurants or other food handling applications, a food preparer or server often has to also handle money. That person may have to constantly wear a glove, take it off, wear a glove, take it off, and so on. Thus, an automated system that aids in glove donning and removal would help guard against transmission of germs and other contaminants to the food.

In a restaurant environment, the use of a protective glove—the purpose of the glove isn't to protect the wearer so much. It's to protect the others from your dirty hands. So it's a little bit different. It's still a barrier but it's a little bit different.

Another notable consideration regarding the subject de-gloving system and method is that the hook members must remain clean and preferably sterile before they get used. So in the process of putting a gloved hand in a system compartment for de-gloving, the dirty glove touches the hook member—then the hook member is contaminated and not readily usable. So the hook member preferably remains to be out of the way initially, then once a gloved hand is placed in the appropriate compartment, the hook member is positioned for de-gloving operation. The hook members are initially kept well away from a hand entry zone into the compartment—to allow ample clearance for clumsy, imprecise hand manipulation of the user who may be weary and tired following a long procedure or period of strenuous work. Or, the user may simply be in a hurry, distracted, or just exercising less than optimum care.

Illustrative Embodiments

Figure 8:
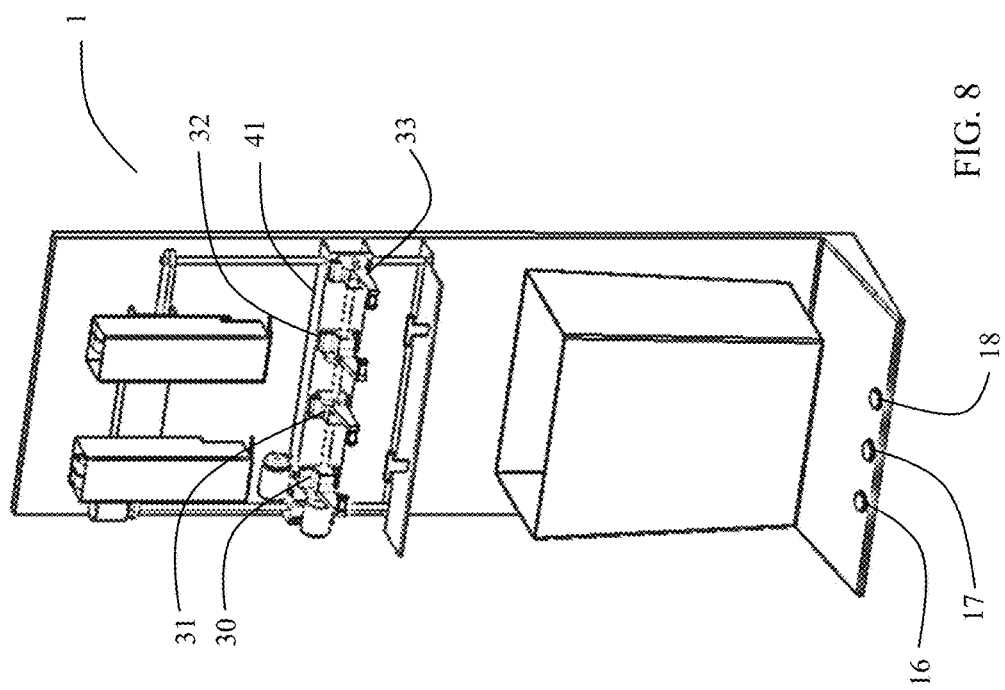
FIG. 8 is an isometric view of a system, shown with the cover removed for clarity, formed in accordance with an alternate embodiment of the present invention.
Figure 9:
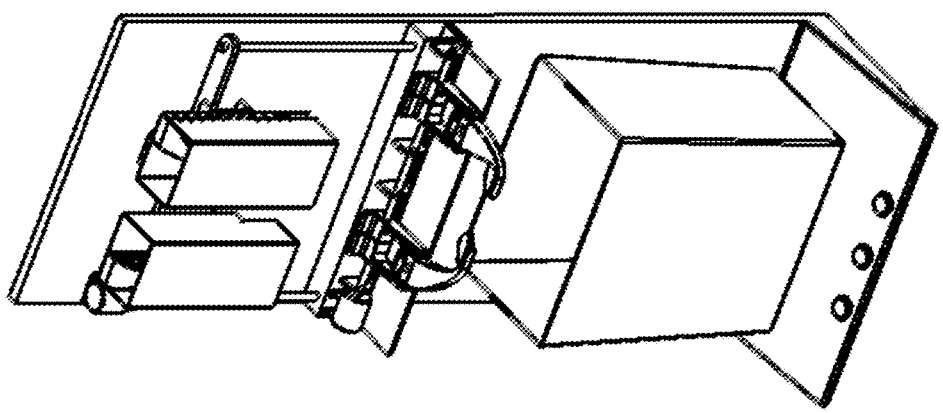
FIG. 9 is an isometric view of a system, shown with the cover removed for clarity, formed in accordance with another alternate embodiment of the present invention.
Figure 10:
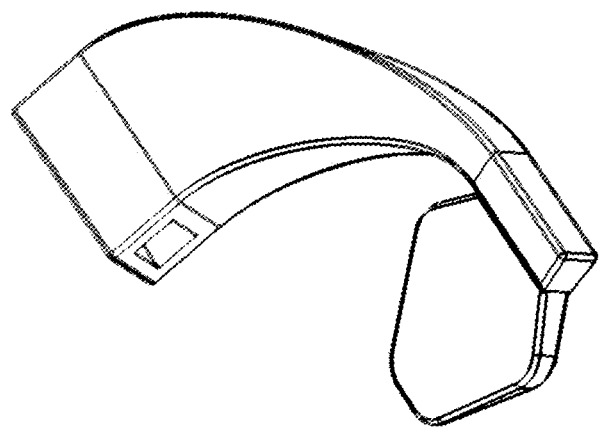
FIG. 10 is an isolated isometric view of glove removing hook members formed in accordance with an alternate embodiment of the present invention, such as used in the system embodiment of FIG. 9.
Figure 10:
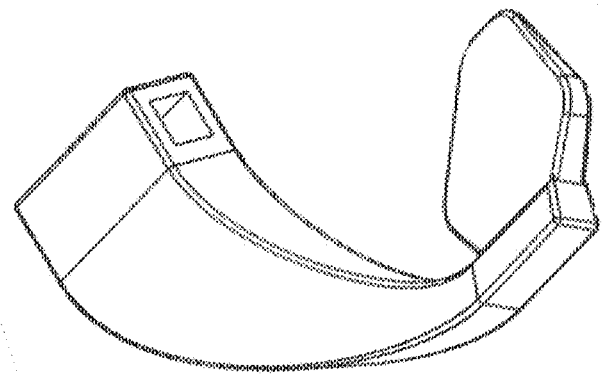

FIGS. 1-7 illustrate one example of a system 1 formed in accordance with an embodiment of the present invention. FIG. 8 illustrates a similar but varied configuration of system 1 formed in accordance with one alternate embodiment of the present invention. FIGS. 9-10 illustrate different aspects of a system 1 formed in yet another alternate embodiment of the present invention similar to the embodiment of FIGS. 1-7, but with hook members configured differently to suit the requirements of a particular application. Indeed, the base system may be the same as in the embodiment of FIGS. 1-7, but with one of numerous differently configured hooks loaded for use in a particular application. FIGS. 11-14 illustrate an altogether different embodiment of a system formed in accordance with the present invention, while FIGS. 15-16, 17-A, and 17-B illustrate still more variations of hook members configured for particularly effective use in system embodiments where extraneous movement of the hook members themselves upon engagement of the glove is minimized to support more manually maneuvered de-gloving action thereafter.

While separately described, various features and aspects of the invention incorporated or realized in one embodiment may be suitably substituted for or interposed in another depending on the particular needs of the intended application. Like features and aspects described in connection with one embodiment may not be redundantly described in connection with another embodiments to preserve brevity and clarity, but are nonetheless incorporated as those skilled in the art will readily recognize.

Referring now to FIG. 1 of the drawings, there is shown system 1 formed in accordance with one exemplary embodiment of the present invention. System 1 is shown with cover 2 in place. Cover 2 is preferably made out of transparent plastic or glass so that the components behind cover 2 and the user's own hands and gloves may remain visible during system operation and use.

Figure 2:
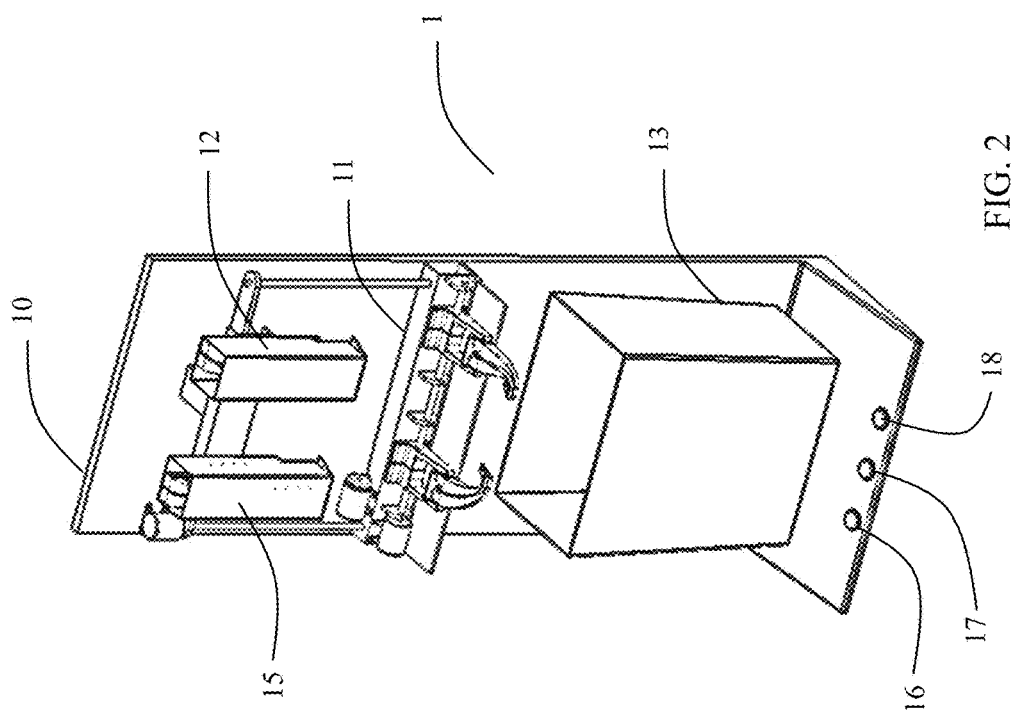
FIG. 2 is another isometric view of the system embodiment of FIG. 1, shown with a cover removed for clarity.

Referring now to FIG. 2 of the drawings, system 1 is shown with cover 2 removed for clarity. System 1 generally includes main frame 10, main mechanism 11, right cartridge 12, left cartridge 15, and trashcan 13.

Trashcan 13 may either be hinged so that trashcan 13 may swing out or be riding on a pair of rails so that trashcan 13 may slide out. Inside trashcan 13 could be a disposable lining.

At the foot of main frame 10 are preferably provided a plurality of switching mechanisms—for example, in the form start button 16, open button 17, and discard button 18 in the illustrated embodiment and application. In addition to voice- or other indirect means of actuation, other direct activation measures known in the art may be suitably provided in place of the foot operated buttons 16 shown. Such activation measures may be provided at any other readily accessible portion of the system for convenient hands-free system actuation by the user employing the arms, head, or other available part of the body.

Figure 3:
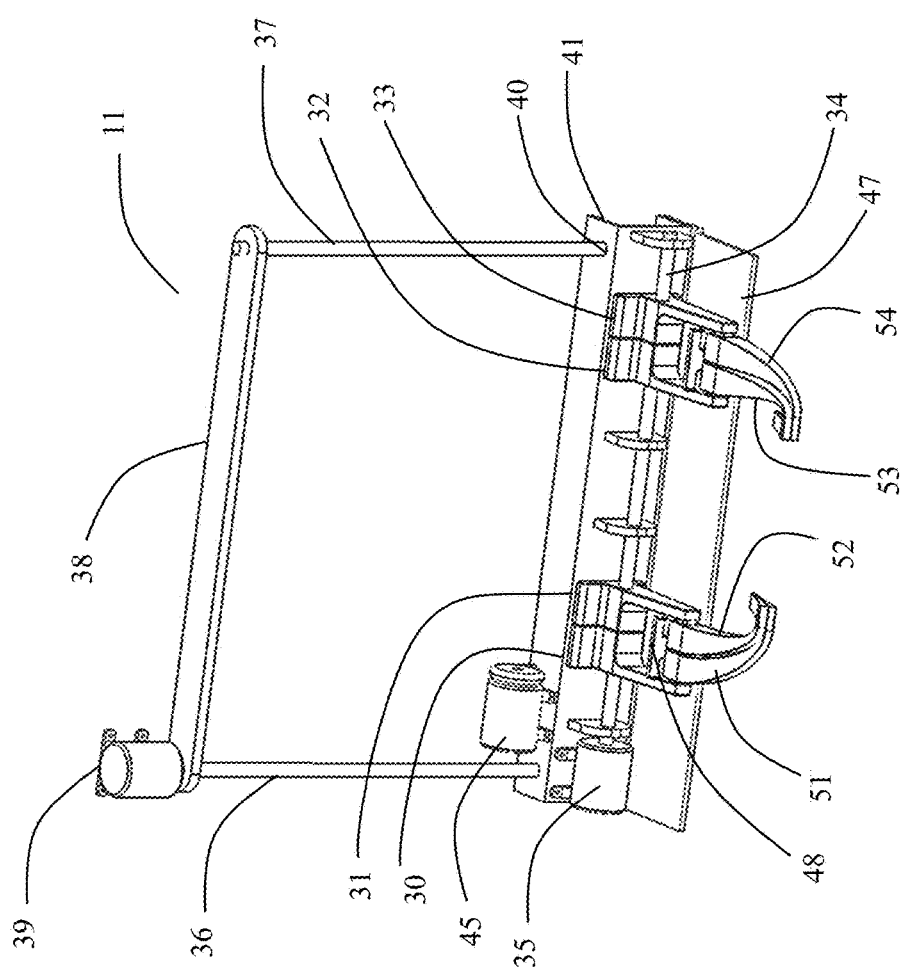
FIG. 3 is an isolated isometric view of a mechanized portion of the system embodiment of FIG. 1.

Referring now to FIG. 3 of the drawings, main mechanism 11 preferably includes in this embodiment a left hook base assembly formed by the combination left hook base A 30 and left hook base B 31, and a right hook base assembly formed by the combination of right hook base A 32, right hook base B 33. Main mechanism 11 preferably also includes a hook assembly body 41, lateral all-thread rod 34, lateral motor 35, left vertical all-thread rod 36, right vertical all-thread rod 37, vertical belt assembly 38, vertical motor 39, air pump 45, splash guard 47, and hook stopper bracket 48.

As described in following paragraphs, the separate hook base components A and B of each left/right hook base assembly cooperatively enable a broadening of a glove's opening which draws the glove material away from contact with the surface of the user's hand at that base assembly, while expanding the clearance for the hand's removal. That is, once the tips of the cooperative hook elements held by the left hook base assembly, for instance, are jointly inserted sufficiently between the glove and hand at that assembly, one or both of the left hook base A component 30 and left hook base B component 31 may be displaced to cause a mutual parting thereof. This draws the respective hook elements away from one another by a suitable distance to stretch the glove's opening wider while pulling at least a portion of the glove material to detach from contact with the skin of the given hand. This detaching, stretching operation aids in the hand's convenient removal from the glove. A similar operation may be effected for the right hand base assembly.

Vertical motor 39 is attached to main frame 10. Left vertical all-thread rod 36 is directly connected to vertical motor 39. Right vertical all-thread rod 37 is synchronized with left vertical all-thread rod 36 using vertical belt assembly 38 so that the spinning action of vertical motor 39 with respect to its rotational axis causes both left vertical all-thread rod 36 and right vertical all-thread rod 37 to spin with respect to their rotational axes substantially at the same rate.

Hook assembly body 41 is formed with insertion holes 40 that are threaded, and these insertion holes 40 mate with both left vertical all-thread rod 36 and right vertical all-thread rod 37. The spinning actions of both left vertical all-thread rod 36 and right vertical all-thread rod 37 cause hook assembly body 41 to move up or down depending on the spinning direction of vertical motor 39.

Lateral all-thread rod 34 is directly connected to lateral motor 35, which is attached to hook assembly body 41. The spinning of lateral motor 35 with respect to its rotational axis causes the spinning of lateral all-thread rod 34, which passes through the threaded holes in left hook base A 30, left hook base B 31, right hook base A 32, and right hook base B 33. Lateral all-thread rod 34 preferably has both clockwise thread and counterclockwise thread so that when lateral all-thread rod 34 spins, depending on the direction of the spin, left hook base A 30 and left hook base B 31 can either move away from or move toward each other, and right hook base A 32 and right hook base B 33 can either move away from or move toward each other.

Left hook upper 52 is attached to left hook base B 31; left hook lower 51 is attached to left hook base A 30; right hook upper 53 is attached to right hook base A 32; and, right hook lower 54 is attached to right hook base B 33.

Left hook base A 30, left hook base B 31, right hook base A 32 and right hook base B 33 are connected to air pump 45 via air tubes behind hook assembly body 41.

Both splash guard 47 and hook stopper bracket 48 remain stationary even when hook assembly body 41 moves up and down with respect to main frame 10 because splash guard 47 is attached to main frame 10 and hook stopper bracket 48 is attached to splash guard 47.

Figure 4:
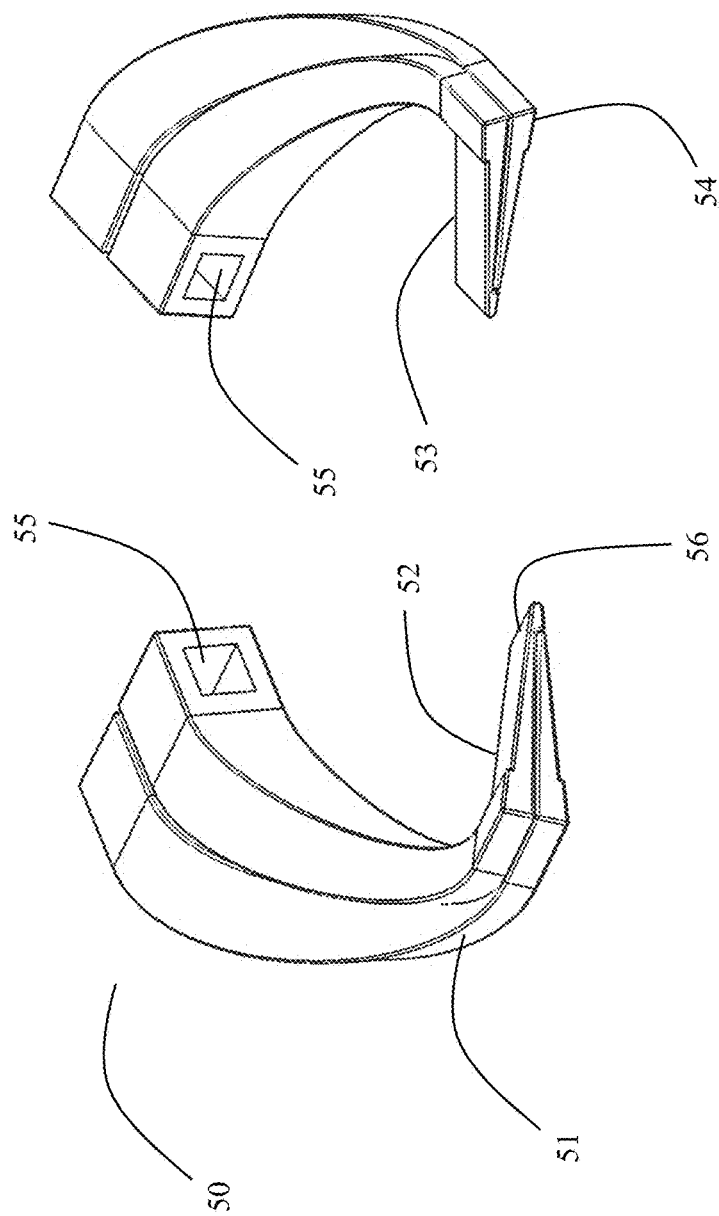
FIG. 4 is an isolated isometric view illustrating examples of glove removing hook members configured for use in the system embodiment of FIG. 1.

Referring now to FIG. 4 of the drawings, there are shown illustrative examples of hook members 50 formed in accordance with one of numerous embodiments depending on the requirements of the particularly intended application. The respective hook members 50 for left and right hand glove removal may be suitably formed with complementary shape and/or orientation depending on certain aspects of the system as implemented for a particular application, such as for instance the configuration and/or arrangement of their hook bases 30, 33. The hook members 50 may be configured with various shapes, contours, and dimensions, and material composition to suit the particularly intended application, but they are preferably configured to extend sufficiently around and down beyond the splash guard 47 to be substantially shielded thereby from the non-disposable hook manipulating parts of the system, such as the hook bases 30, 33 and their supporting and their driving/controlling structures. Each of the hook members 50 is preferably formed in this embodiment as multi-piece assemblies (each including multiple disposable hook elements such as the lower and upper elements 51, 52 and 53, 54 described for the left and right hook members 50 in following paragraphs) to accommodate the widening operation for the glove's opening, where the hook elements are drawn apart by a suitable amount by their hook base components A, B.

But each hook member 50 in certain alternate embodiments may be formed by a unitary disposable hook component (such as described in connection with the embodiment illustrated in FIGS. 9-10). In such embodiments, the unitary hook component may engage the glove to draw the engaged portion away from the user's hand, either by displacing the hook component relative to the hand or manipulating the hand while the hook component remains stationary. But the glove opening itself is not widened about the hand in the manner that multiple cooperating hook components may by engaging and mutually displacing to stretch opposed portions of the glove apart.

The hook members, or hooks, 50 for the exemplary embodiment illustrated in FIG. 4 include left hook lower 51, left hook upper 52, right hook upper 53, and right hook lower 54. Left hook lower 51 and left hook upper 52 are preferably nested, adjacent to each other, and may be lightly connected for handling purpose but easily separated when pulled apart for individual deployment/use. Insertion hole 55 preferably has a groove formed inside that is greater in size than the insertion hole 55 opening (to accommodate retentive engagement by a tab protruding from a member inserted in the hole 55). Left hook upper 52 has an internal channel that allows movement of air from insertion hole 55 to air hole 56. Preferably, right hook lower 54 is a mirror image of left hook lower 51, and right hook upper 53 is a mirror image of left hook upper 52.

All or part of each hook member may be disposably formed. While the entire hook member may be disposable, and therefore detachably coupled to the main mechanism, a portion of the hook member may be detachably coupled to the remaining portion in certain alternate embodiments. Following a de-gloving operation only the detachable portion (such as the tip or a sheath like full or partial cover portion thereof) may be disposed of, with the remaining portion of the hook member remaining in place for subsequent use with a replacement of the dispose portion, in those embodiments.

Figure 5:
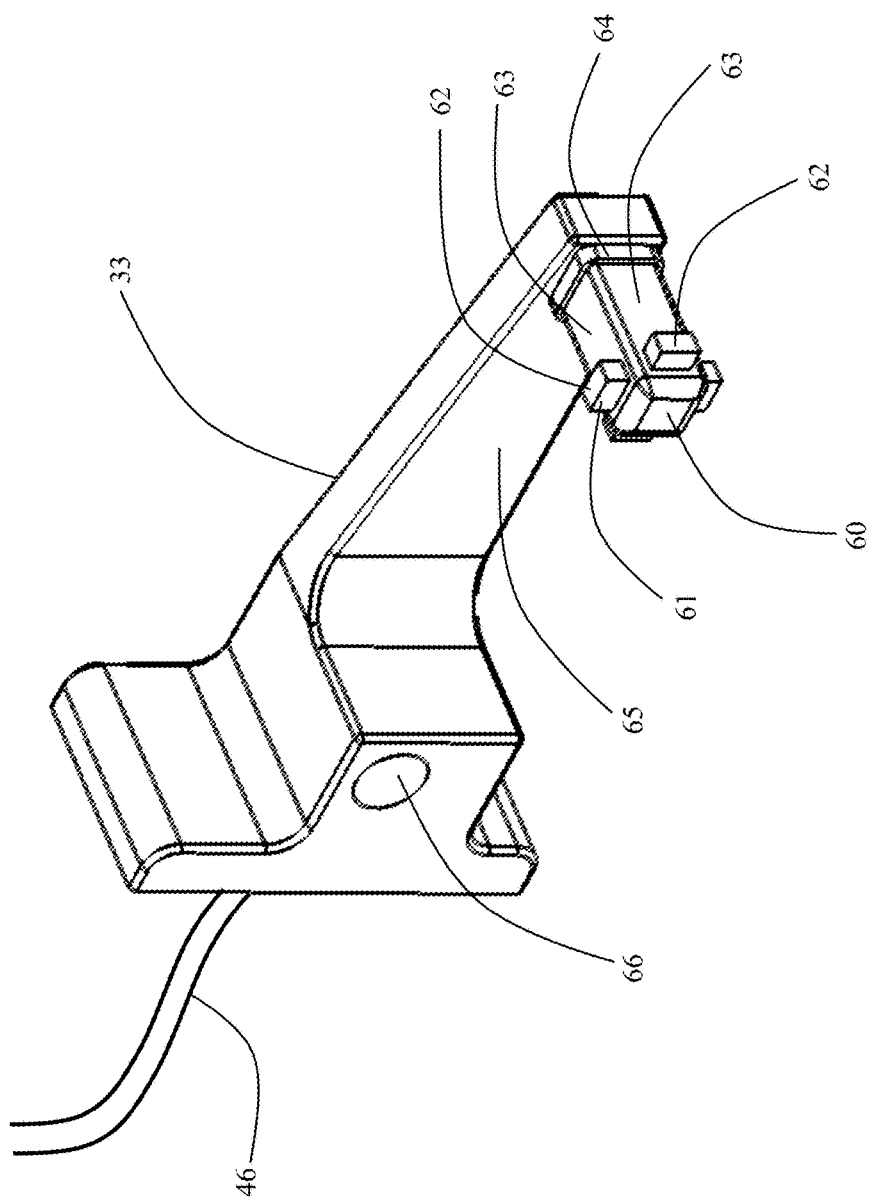
FIG. 5 is an isolated isometric view of a hook base portion for releasably holding a hook member in the system embodiment of FIG. 1.

Referring now to FIG. 5 of the drawings, right hook base B 33 is shown for illustration. Right hook base A 32 is a mirror image of right hook base A 33. Left hook base A 30 is identical to right hook base A 32 and left hook base B 31 is substantially identical to right hook base B 33.

Right hook base B 33 is preferably formed with an internal air channel, so that air supplied from air pump 45 via air tube 46 can travel inside the right hook base B 33 from air tube 46 to base tip 60. When enough air pressure builds up inside base tip 60, tabs 61 protrude out as shown. Without air pressure, spring loaded tabs 61 go inside and remain inside base tip 60. When tabs 61 are inside base tip 60, tab top surfaces 62 are flushed with base tip side surfaces 63 on all four sides of base tip 60.

Before right hook lower 54 slides on to base tip 60, air pump 45 is stopped and no air is supplied to right hook lower 54 and tabs 61 are inside base tip 60 and tab top surfaces 62 are flushed with tip side surfaces 63. Base tip 60 slides into right hook lower 54's insertion hole 55 until base tip shoulder 64 stops the sliding. After right hook lower 54 is stopped, air pump 45 is activated, and the compressed air delivered to right hook base B 33 causes tabs 61 to protrude out and go into the grooves inside right hook lower 54, thereby locking right hook lower 54 in place with respect to right hook base B 33.

Base tip shoulder 64 is preferably configured to be slightly larger than both base tip 60 and insertion hole 55 so that even when right hook lower 54 is pushed fully into the right hook base B 33, a gap remains between right hook lower 54 and base inner surface 65.

The shape, size, number, relative dimension, and other such configurational features shown for the tips 60 and tabs 61 formed on the hook base components, as well as for the corresponding insertion holes 55 formed on hook member elements, provide illustrative examples. They may be suitably varied according to the needs of the particularly intended embodiment and application. Likewise, the pneumatic actuation of tabs 61 provides but one example of the various modes of automated actuation which may be employed. Other known modes of actuation, such as mechanical, electromechanical, magnetic, electromagnetic, or the like may be suitably employed depending on the needs of the particularly intended embodiment and application. In certain alternate embodiments, moreover, the tabs 61 of the hook base components may be eliminated altogether in favor of other suitable means such as external latching mechanisms to effect the releasably locked retention/fastening of hook member elements to their respective hook base components.

Figure 6:
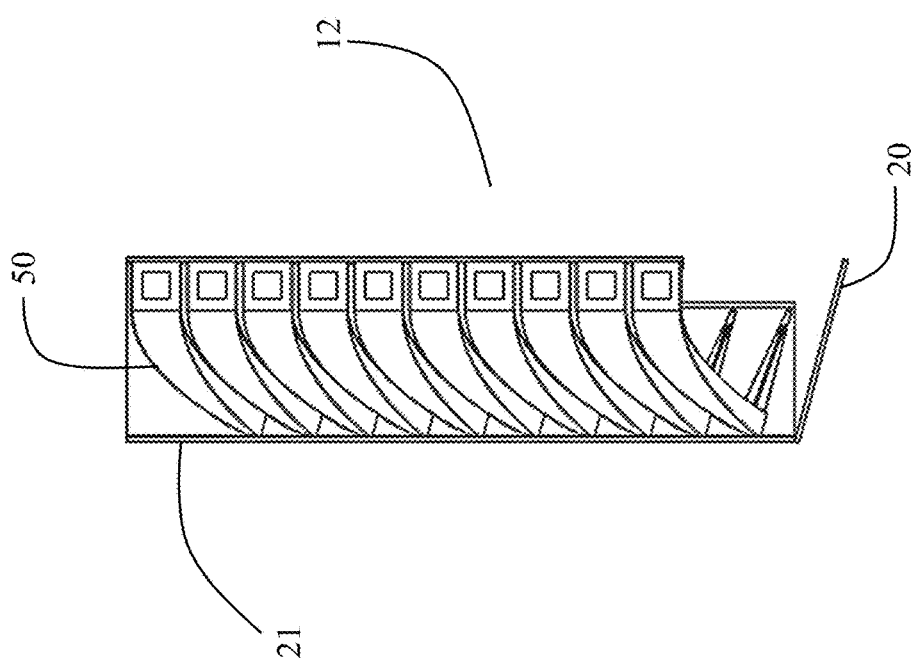
FIG. 6 is a cutaway side view of cartridge with a plurality of hook members stacked inside the cartridge in accordance in the system embodiment of FIG. 1.

Referring now to FIG. 6 of the drawings, a transparent side view of right cartridge 12 is shown with a stack of hooks 50. Cartridge cover 20 is spring loaded so that unless forced open, cartridge cover 20 remains closed so that airborne fluid droplet projectiles coming up from the below cannot reach the hooks 50 that are inside cartridge body 21. Cartridge cover 20 can be pushed open by hooks 50 when hooks 50 are pulled down by of any of left hook base A 30, left hook base B 31, right hook base A 32, and right hook base B 33.

When a set of bottom most hooks 50 are pulled out of cartridge body 21, the remaining sets of hooks 50 drop downward to advance to the bottom most position, preferably by gravity assist.

Figure 7:
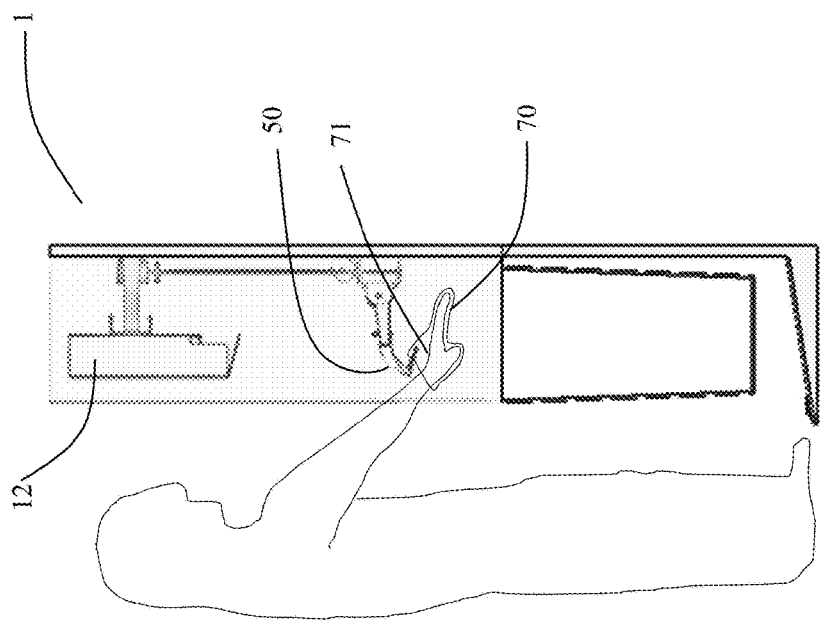
FIG. 7 is an illustrative side view of the system with a user utilizing the system embodiment of FIG. 1.

Referring now to FIG. 7 of the drawings, when a user stands in front of and facing system 1, the user may put one or more of his/her gloved hands inside the system 1 through the opening of cover 2. Then the user manipulates each gloved hand to engage the hooks 50 to insert between the gloves 70 and dorsal sides of the hands 71. The user has an unobstructed view of hooks 50 from the user's point of view because both left cartridge 15 and right cartridge 12 are sufficiently out of the way and not blocking the line of sight.

Referring now to FIG. 8 of the drawings, with cover 2 removed for clarity and with system 1 configured in accordance with an alternate embodiment of the present invention to provide dual glove removal measures for removal of both left and right hand gloves concurrently if necessary. System 1 is shown in its initial state, with hook assembly body 41 in the initial waiting position and hooks 50 not yet retrieved from either the left cartridge 15 or right cartridge 12. Left hook base A 30 has been separated from left hook base B 31, and right hook base A 32 has been separated from right hook base B 33.

Sample Sequence of Operation:

Initial State:

Hooks 50 are inside both left cartridge 15 and right cartridge 12.

Hook assembly body 41 is disposed mid-way between trashcan/waste receptacle 13 and the bottom of left cartridge 15 and right cartridge 12.

Left hook base A 30 has been pulled away from left hook base B 31, and right hook base A 32 has been pulled away from right hook base B 33.

Air pump 45 is not activated.

Hook Retrieval Stage:

The user presses start button 16 with his/her foot.

Start button 16 activates vertical motor 39. The spinning of the vertical motor 39 rotates both left vertical all-thread rod 36, right vertical all-thread rod 37, which in turn bring up hook assembly body 41. Vertical motor 39 stops spinning the rods when base tips 60 are aligned with insertion hole 55.

After hook assembly body 41 is stopped, lateral motor 35 activates, which causes lateral all-thread rod 34 to spin along its rotational axis.

The spinning of lateral all-thread rod 34 causes both hook base A 30 to move closer to left hook base B 31 and right hook base A 32 to move closer to right hook base B 33.

The spinning of lateral all-thread rod 34 continues until base tip shoulders 64 touch hooks 50.

After lateral all-thread rod 34 stops spinning, air pump 45 is activated and compressed air is delivered to hook base A 30, left hook base B 31, right hook base A 32, and right hook base B 33. The compressed air causes tabs 61 to protrude out and lock hooks 50 to base tips 60.

After hooks 50 are locked to base tips 60, vertical motor 39 spins in opposite direction, which lowers hook assembly body 41.

Vertical motor 39 spins until hook assembly body 41 reaches splash guard 47.

System 1 waits for the user to insert the front segment of hooks 50 between his/her dorsal sides of the hands 71 and the gloves 70.

Small amount of air may be generated through air hole 56 in certain applications to help separate gloves 70 and dorsal sides of the hands 71.

Hook Open Stage:

After the user inserts the front segment of hooks 50 between his/her dorsal parts of the hands and the gloves, s/he presses open button 17.

The pressing of open button 17 activates lateral motor 35 and both left hook upper 52 begins to move away from left hook lower 51 and right hook upper 53 begins to move away from right hook lower 54. This continues until the hooks 50 widen the opening of the gloves to be slightly wider than the width of a typical user's hands. At this point, the user takes his/her hands out of the gloves and press discard button 18 with his or her foot.

Discard Stage:

When discard button 18 is pressed, air pump 45 stops pumping air and vertical motor 39 spins and slightly raises hook assembly body 41 until hooks 50 are aligned with hook stopper bracket 48. This causes the tip of hook stopper bracket 48 to be sandwiched between hooks 50 and left hook base A 30, left hook base B 31, right hook base A 32, and right hook base B 33.

After hook assembly body 41 stops moving, lateral motor 35 begins to spin and pulls both left hook base A 30 away from left hook base B 31 and right hook base A 32 away from right hook base B 33. Because hook stopper bracket 48 stops hooks 50 from being separated, eventually all hook bases are completely detached from hooks 50. With nothing holding from falling, hooks 50 and gloves 70 fall into trashcan 13.

After hooks 50 fall into trashcan 13, vertical motor 39 spins and raises hook assembly body 41 to the initial position.

Meanwhile, gravity pulls down unused hooks 50 in left cartridge 15 and right cartridges 12 to the lowest allowable position in the cartridges for the next operation.

FIG. 9 illustrates a system 1 formed in accordance with another alternate embodiment of the present invention. This embodiment is similar to the embodiment illustrated in FIG. 2. It employs a pair of hooks of different configuration, such as the exemplary hook members illustratively shown in FIG. 10. Unlike the embodiment illustrated in FIGS. 3-4, one unitary hook member may be employed at each of the left and right glove removal sides (rather than the multi-piece assemblies formed by nested and mutually displaceable hook elements A, B at each of the left and right glove removal sides) for a simplified implementation without the widening operation for the glove's opening. Each unitary hook member may be configured as shown with suitable configuration for retentive support and fastening between hook base components A, B at each of the left and right glove removal sides. Where the particular requirements of the intended application permit, each unitary hook member in this embodiment may also be supported and fastened from one side by either of the hook base components A, B, obviating the need for the other component B, A. Depending on the particular requirements of the intended application, implementation factors such as the material, construction, and type of gloves to be removed, the required speed of removal, expected dexterity of the user, or the like, the glove removing hook members may be formed with any suitable shape, material, structure, and other configurational features.

Examples of Alternative Features which May be Suitably Incorporated in Various Other Embodiments and Applications of the Subject System and Method:

1. Instead of foot buttons, sensors could detect the presence of hands to activate and operate the system.
2. Instead of two pairs of hooks, the system could have a single pair of hooks.
3. Instead of discarding the hooks after the usage, the hooks could be kept.
4. Instead of hooks separating to stretch open the gloves, the hooks are slightly wider than a typical human hand such that the action of inserting the hook between a dorsal part of the hand and glove stretches open the glove for easier removal of the hand from the glove.
5. Instead of a hook's base tip 60 going inside hooks insertion hole 55, the hook's base may have an insertion hole and the hook can have a positive protrusion that can go inside hook base's insertion hole. This can reduce the size of the hooks.

The particular mechanisms employed in the disclosed embodiments to selectively displace and relatively position the hook base assemblies provide but one illustrative example. The combinations, configurations, and arrangements of motors and rods shown may be varied or replaced with other suitable measures known in the art to accommodate proper operation of the particularly intended embodiment and application. For example, the number, type, and locations of the motors and/or rods for transmitting mechanical movements generated thereby may be varied in certain alternate embodiments. What is more, other mechanical, electromechanical, magnetic, electromagnetic measures, or the like known in the art may be suitably employed depending on the needs of the particularly intended embodiment and application.

Turning to the alternate system embodiment shown in hand drawn FIGS. 11-14, the system includes a box-type housing 2' having a lid 3'. The box housing 2' is big enough to have a sizeable compartment, and inside the box, a wall 4' bounds one side of the compartment. A mechanical box 9' preferably contains suitable electro-mechanical hardware known in the art for controlling the various movements of components carried out during de-gloving operation.

That is, a top surface 9' of a back-enclosed chamber is provided at least the major electro-mechanical hardware is disposed. The system also includes a plurality of hook members, or hooks, referenced by RA, RB (Right A, Right B).

There is illustrated: a system (or device) 1', glove remover 2', device lid 3', trash compartment 8', hook LA 20', hook LB 21', hook RA 22', hook RB 23', hook cover 7', mechanical compartment 9', and a hook vertical door 5', hook openings 10', trash compartment 8', motion detector 11', external lid opener 12'. Upward direction 13', glove opening 25' (FIG. 12), first leg 24', back of the hand 30', left glove 29', right glove 60' (FIG. 12), stream of air 28', tip pole 32'. Also shown are a direction A 40', direction LB (left back) 41', pinky 43', thumb 42', direction RA 50', direction RB 51'.

Unless otherwise noted, each identified portion/component disclosed in the various embodiments disclosed herein may be formed of any suitable material and/or configuration known in the art.

When the user wearing the glove wants to remove the glove, he/she may wave their hand(s) in front of the box. Initially, the box remains in its normally closed configuration, where the lid is completely closed. Preferably, the user may simply wave their hand in front of the motion detector, or press down on the external lid opener by foot actuated pedal, for instance, for hands free, automatic actuation to open the lid.

A motion detector is preferably disposed outside of the box. It is preferably disposed on the front exterior surface of the box, near the top for optimally clear view of the hand. The soiled gloved hand need not touch the box. Other suitable actuation measures, such as a foot operated switch or sound operated switch, or the like may be employed in this regard.

Figure 11:
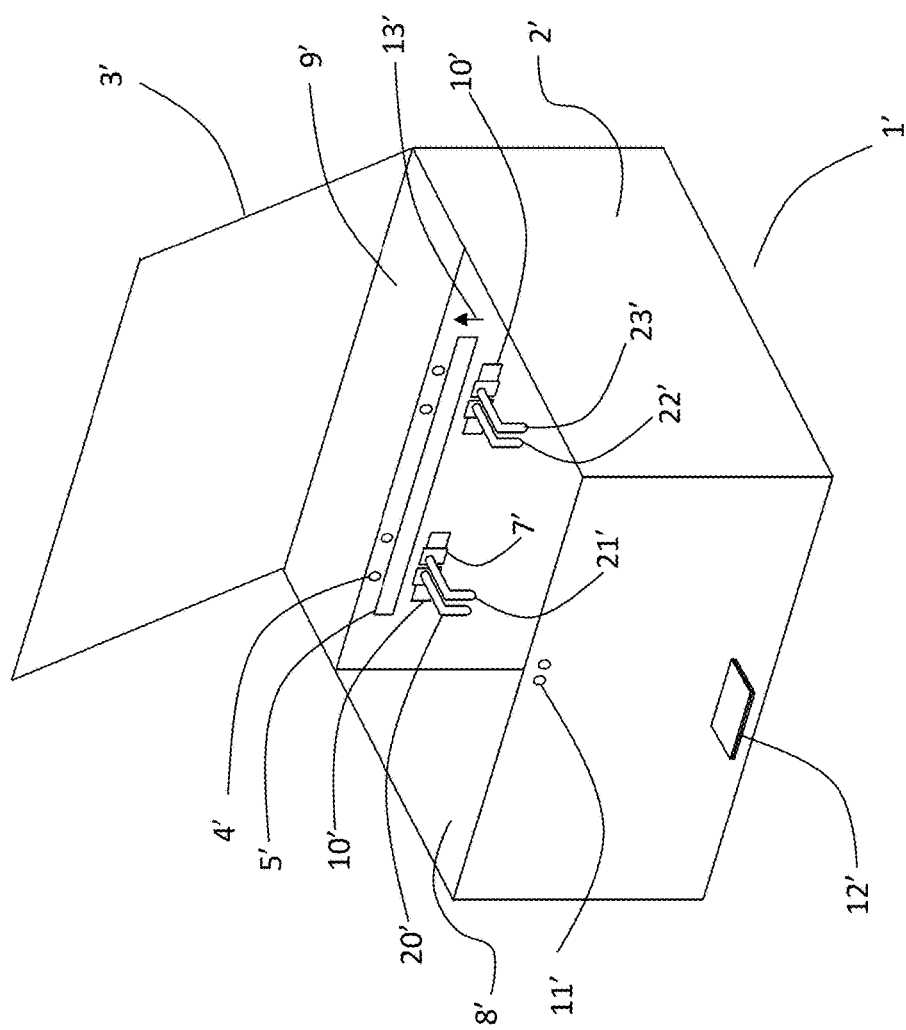
FIG. 11 is a perspective view schematically illustrating a system formed in accordance with another alternate embodiment of the present invention.

So once the lid is opened, the RA, RB, LA . . . all such hooks are positioned inside the mechanical compartment. In FIG. 11, the RA, RB hooks are all shown out in the open. But preferably, they would be contained inside the mechanical compartment 9', and the opening would be covered by hook vertical door. The vertical door actually covers the opening so when the lid is opened, the hooks are drawn out of the way and not readily within view.

The vertical door 5' moves up and down. Preferably, it slides up and down, much like a garage door, for example. Upon the door's opening, the hooks emerge (displace or extend out) and take their initial engagement positions. The door 5' serves as an access cover for the hook windows. As shown, the door 5' may be retracted underneath the surface of compartment 9', so that only a portion is exposed (essentially the tip of it), much like a conventional sliding door in structure and function.

If the door were fully extended, it would slide out of the pocket/compartment into which it retracts, to then hang over and cover the openings that the hooks come out of. When it is not in use, the vertical door closes in this particular embodiment much like a garage door would, and at that point, the hooks are concealed completely inside the mechanical compartment. This keeps the hooks contained and away from potential contamination prior to use.

When discarded gloves and/or spent hooks need to be thrown out, the unused hooks are protected against exposure to the space outside its protectively enclosed compartment. When a user is putting his or her hands into the box, his/her contaminated glove is thereby kept from touching any new, unused hook with their gloved hand inserted into the area of operation.

During typical operation of the system, when the user first approaches and waves a hand or depresses a foot pedal to open the lid 3', they will not see anything initially except an empty compartment or an empty chamber. The door 5' at that point is preferably fully closed. But once they put their hand inside, the door preferably opens automatically, responsive to suitable sensing measures such as a motion detector 4'. When the motion detector or other sensor detects the hand, the door opens. When one extends the hand far enough into the compartment, the motion detector triggers/actuates the door 5' to open, and the hooks project out through the exposed opening.

At that point, the user's hand is situated somewhat vertically. So the hooks come out to almost touching the top of the hand. Preferably, there's enough room between the hook and front wall of the device/system that the hooks need not actually contact the hand when fully projected out. The user is able to see the hooks come out, and keep the hand so that it stays clear of the hooks until they're fully projected. And then, the user may manually position and orient the base of his/her hand relative to the hooks, such that the hooks engage the glove's open end and insert underneath between the glove and covered skin.

Figure 12:
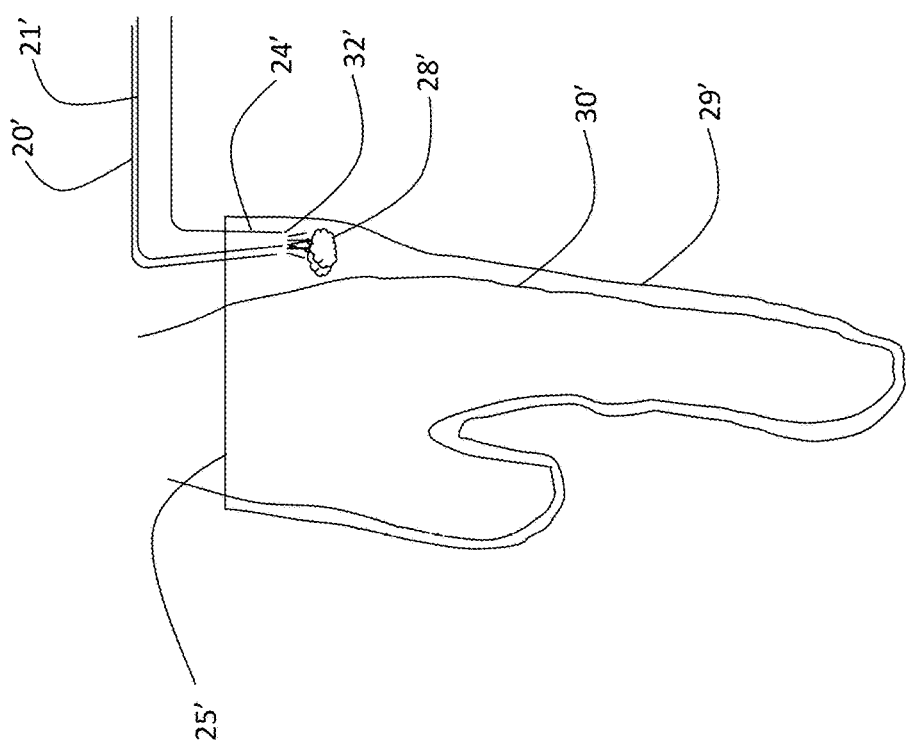
FIG. 12 is an elevational view schematically illustrating a portion of the system shown in FIG. 11, engaging a glove worn on a user's hand in hooked manner.

The hook is configured in this illustrated embodiment to extend out horizontally and bend near its terminal end. There's a substantially 90 degree bend in a transverse directly to form an approximate L-shape 2' (as shown in FIG. 12). The bent extensions form feet-like portions.

In certain other embodiments, the user may place the hand on the opposite side of the hook, with the hook then automatically displacing toward the gloved hand to sense the hand. Depending on the particular embodiment, then, either the user may move the hand to the hooks, or the device moves the hooks to the hand. But it's usually simpler for the user to manipulate their hand.

In yet another version, the hook may actually follow a circular route. The hook may be displaced to make an approximate 180 degree turn from its original position to approach the hand and glove from a convenient, optimal angle to insert between the glove and wrist area at the base of the hand.

So the hook displaces pivotally in this case. It swings around. It swings up and over, and down into position to grip the edge of the glove away from the hand. The hook's terminal end is preferably shaped like a wedge so that it may easily pry into the space between the glove and hand. The user in any event puts the edge of the glove, typically positioned over his or her wrist, and causes it to catch on the bent ends of the hooks. Preferably though not necessarily, a puff of air is generated through the hook's tip into that space between the glove and wrist.

The puff of air is preferably timed for right before the hook engages the glove. This could be timed or even could be manually operated, using suitably accessible and actuated control measures. Such a puff of air would actually help to separate the glove from the hand and thereby create a gap/opening therebetween. If the puff of air is too strong then there could be unwanted splattering of the noxious/contaminant material from the outer surface of the glove. So the puff of air (or other suitable gaseous burst) is preferably gentle.

The puff of air would preferably be expelled directly from or near the hook's tip. If the puff of air cannot be precisely timed, it may be delayed until the given hook has sufficiently engaged the glove because generating the puff beforehand may not be sufficient to separate (and open space between) the glove and the hand/wrist. The hook may have to be manually worked in to separate the glove and hand/wrist, and then once situated there, have the puff blow the space further open. This would serve to create a slight aerodissection.

Depending on the intricacies involved in the particularly intended application, the timing of this puff of air may prove quite tricky. It may be preferable in most applications to manually operate or manually trigger the puff. Once the user is in position, he/she may say, "Hey do it" or provide other suitable user-prompt.

A sensor may be suitably employed to help provide precise timing. In certain applications, a touch or pressure sensor may be employed toward that end. For example, as the glove is pulled off against hook once the hook is in place between the glove and skin, the sensor may be triggered to actuate the air puff. The sensor may be situated in that case for instance inside of the elbow-like bend. When the user starts pulling the glove material against the hook, then its tip is sufficiently deep inside the glove for the glove's edge to touch and automatically trigger the puff.

Alternatively, such sensor may be located at or nearer to an attachment base of the hook because at least the tip portion of the hook is preferably disposable. A sensor would be cost intensive, so it is preferable to reuse it. In that regard, a non-contact sensor such as an optical sensor may be preferable to avoid inadvertent sensor contamination.

Regardless of the actual type of sensing technology employed, it is preferable to include a suitable way to automatically sense that the hooks have engaged deeply enough inside and underneath the glove material that an air puff may be safely blown without making a big mess.

As the system puffs the air, the hook begins to more fully separate the glove from the protected skin, as shown in FIG. 12. Although preferable, such puff of air generation is not necessary in every embodiment and application. One may manually effect the separation by working the hands gently back and away from the hooks against which the glove retentively engaged.

Once they adequately engage the glove, the hooks are moved by the system to separate from one another. In the illustrated embodiment, they move laterally parallel to the dorsal of the user's hand. So when they initially emerge for use, these hooks are disposed side by side, close together, at about the middle of the compartment horizontal. Once they've safely engaged the glove, they starts to separate laterally. This serves to gently stretch and begin the process of removing the glove from the hand.

Having multiple points of separation tends to ease the force of removal. This is particularly helpful to the extent that removal is automatically driven. One point of contact for a pull requires a greater tugging force at there, as opposed to two separate points over which to distribute the force, easing the glove's removal.

It is preferable to mutually separate the hooks front to back as well as side to side. This parting separation serves to create a larger, wider air space between the skin and glove. This induces separation between the glove and the hand, even where the skin underneath the glove is sticky from the perspiration, as is the case after such extended use as during a surgical procedure.

So this basically enlarges the glove's opening—or the mouth of the glove—so that the user may more easily pull the hand out without stretching and sling-shotting any contaminant material from the glove. The glove's stretched state is reflected in FIG. 13 (which shows a top-down view). The glove at this point is stretched away from the hand—or the wrist of the user. Now the user is able, after getting to this configuration of FIG. 13, to pull his/her hand out.

Now, the finger portions of the glove may follow the user's fingers out. But that would normally be acceptable since as the glove's finger portions follow outward, they are naturally turned inside out. Any contaminant on the outer surfaces of these finger portions will either drip into the disposal trashcan/receptacle underneath or be enclosed and trapped within the pouch-like formation of the inside-out-turned finger portions of the glove. Whatever material shoots out due to elastic flinging at that point will shoot 'out' internally within that pouch-like formation. The contaminant material at these portions is thereby self-contained.

This is consistent with safe practices when one removes a glove manually. One normally attempts to do just that: remove the glove by gently pulling it inside out as much as possible. This is to essentially enshroud the noxious material while pulling the hand and fingers out of the glove.

There may be numerous different variations of the system's components and configurations from that shown, depending on the requirements and resources of the particularly intended application. Here, the current drawing illustrates an opening where a user may see into or through a cover, so the space where glove removal takes place is near completely contained. There might be a certain slit formed on the side of the box, for instance, where the user may pass a hand through, and the top might have a clear opening—or may include a transparent wall/window that one may see through to either engage the hook or see that the hook is engaged in the glove, and so on.

In the simplified schematic views shown, the hook and other mechanical components are shown for illustrative and explanatory purposes near the top opening of the box-like housing structure of the device/system, but it may be preferable in certain embodiments and applications to place them deeper into the housing's compartment to provide greater margin for error. This may be preferable, for instance, to guard against the case of inadvertent splattering projection of contaminant material upwards (to potentially escape out of the otherwise contained compartment).

Figure 13:
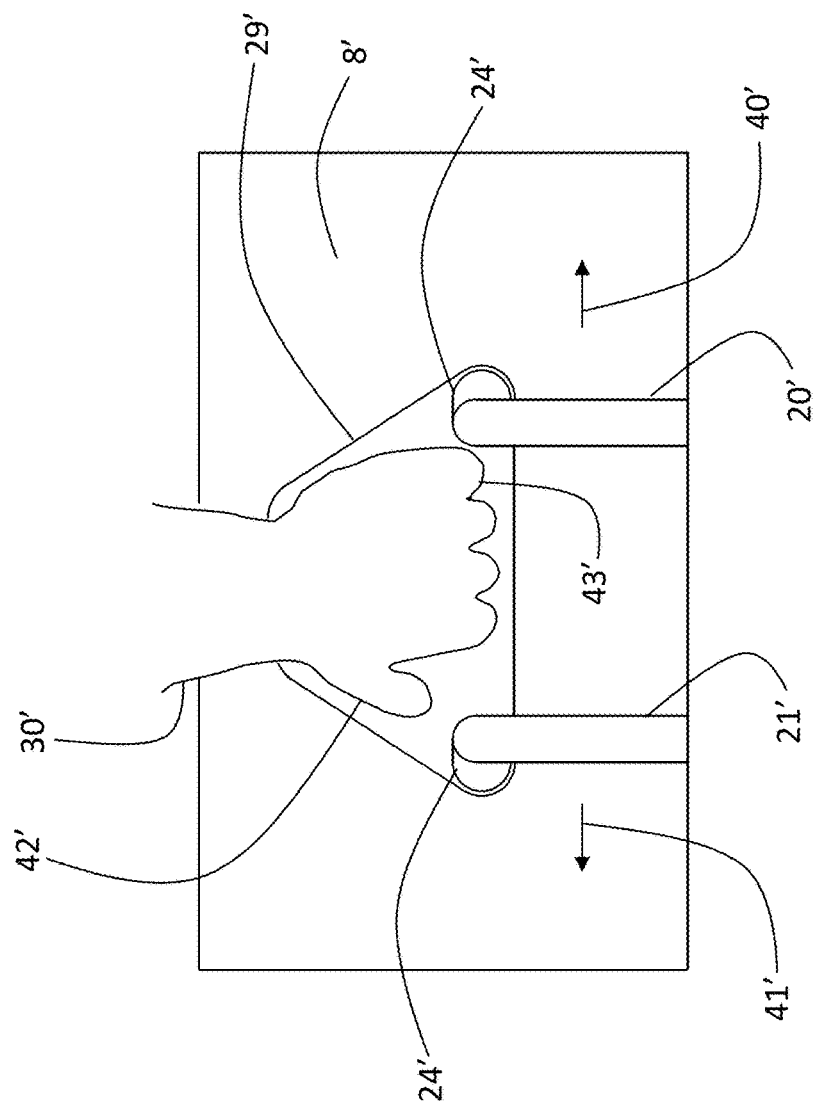
FIG. 13 is a plan view schematically illustrating a left hand version of the portion, as shown in FIG. 12, hookingly engaging a glove worn on a user's left hand.
Figure 14:
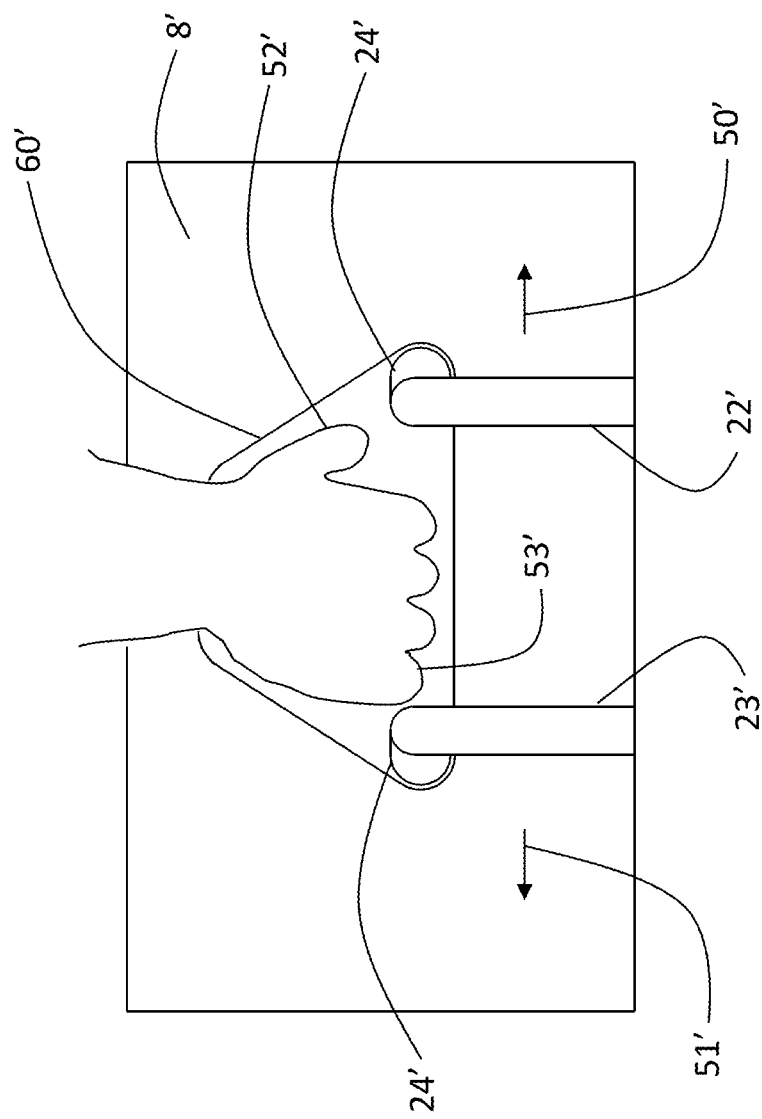
FIG. 14 is a plan view schematically illustrating a right hand version of the portion, as shown in FIG. 12, hookingly engaging a glove worn on a user's right hand.

Preferably, the housing provides substantial self-containment. The walls are enclosed as much as possible. FIGS. 12-14 show in each embodiment the user's hands going in from the top, but they could also go in from the front in different embodiments and configuration (such as illustrated in preceding embodiments). That is, the mechanical components shown may be turned 90 degrees or the like in alternate embodiments' configurations so that the user may insert the gloved hands from the front. To avoid forward splattering—or retrograde splattering when facing the box—suitable measures may be employed to block the frontal opening as much as possible while permitting freedom of hand manipulation and visible access into the compartment where de-gloving takes place.

In certain front-access embodiments (such as variously illustrated in FIGS. 1-10), where instead of inserting hands top down, the hands are inserted front to back, the hooks preferably are at least partially of substantially U-shape to provide effective grabbing of the glove. The U-shaped portions of the hooks would grab the glove front to back and when the user pulls the hands back—retract it back towards the user—then any contaminant material on the outer surface of the glove would drip underneath. With the front substantially open to permit this frontal access, a horizontal window may be formed to be elevated, or provided with an extended disposable bucket or a tray.

Alternatively, a sheath or other flexible curtain, or membrane-like component may be used. A sheath that is somewhat rubbery so that when it goes in, it creates/preserves a barrier may be used. The sheath would shield the user against much if not all of any retrograde splatter towards the individual. Since the sheath could be contaminated by contact of the gloved hand, measures may be necessary in such cases for either disposable sheaths or sheaths formed with suitably configured openings to avoid contact.

In any event, once the glove is removed and the user has pulled the hand out, the glove remains stretched out—since it's still on the hooks which are keeping its stretched. The glove is not going to readily fall off at this point. To dispose of the glove, the hooks may again be drawn towards one another gently to un-stretch the glove, and doing so gently and gradually enough to mitigate any sling-shot projection of material therefrom. That is, the glove's stretching tension is gradually released until the glove drops off.

In the illustrated embodiment, the hooks too (or at least the terminal end portions thereof) are ejected and disposed of with the gloves. This eliminates the risk of contaminating a subsequent user if the hooks are re-used. The hooks may be formed of plastic, wood, even metal, or any other suitable material that provides sufficient properties (like strength and rigidity) to serve the hooking and supporting function for a given glove. They are preferably also of sufficiently economic material composition and structural configuration to be formed and disposed of in bulk.

In healthcare settings like hospital institutions or hazardous material clean up and handling settings, re-sterilization of the hook members may not be a plausible option. But in other settings like food handling and the like, sterilization and re-use of the hooks may be plausible. So there may be different variations in this regard, depending on the particularly intended application.

One way to protect a hook member itself from contamination between repeat uses is to place a sheath or cover on a permanent hook (or at least a multi-use hook). But that could be prohibitively complex and expensive to manufacture in many applications, more so than simply forming each hook to be disposable.

The hook could be thrown away in its entirety if the hook is made out of plastic or other such readily available and inexpensive material. Using a sheath, such as with scopes that enter patients' bodies, tend to be complex and expensive, not only in terms of manufacture but also in terms of regulatory compliance. Disposable plastic hooks are preferably stacked, and perhaps even nested together, in a cartridge with many hooks, because once you throw away so many hooks, you have to replenish it. The cartridge may be suitably configured like a carousel almost, or like a machine gun clip.

Like the cartridge, the overall system minimizes and simplifies the requisite user maintenance actions. The various aspects of system upkeep and use are preferably kept user-friendly—for simple and consistent utilization by the nursing staff, the hospital staff, the Operating Room staff— who may be exceedingly exhausted at the end of a long, tiring day. The self-contained simple cartridge it would be simply loaded into the appropriate compartment, the discarded waste container's liner may be easily replaced. Normal operation would typically just require these two main actions, with little need for complicated directions for proper use. The user need only put a cartridge in to reload and to take out and replace a filled waste container, with the filled container bag being dumped into biodegradable trash depository.

When the user is de-gloving horizontally (simply pulling the hands out from the gloves front to back), then it's normally acceptable for a glove to remain on the hooks because the hooks and glove may then be dropped to discard everything together. Preferably, suitable measures are employed to protect the compartment surface behind and around the hooks from contamination. This is the surface through which the hook admission window is formed. The admission window is preferably larger than the hooks themselves because the hooks have to pass through them. Since the hooks are connected to arm-like hardware which extends, holds, and moves the hooks as needed during the de-gloving process, the surrounding window opening may allow for unwanted contaminant material infiltration into the storage chamber for other yet-to-be-used hooks.

This exposure to contaminant infiltration exists to the extent of the window opening's position relative to the 'active' area where the de-gloving actually takes place. Obviously, the closer it is to this active area, and the lower it is relative to that active area, the greater the likelihood of contaminant (referring generally herein to any type of noxious and potentially harmful material ending up on the outer surface of a used glove) dropping or being flung during the de-gloving process in through the window opening around the hook and hook holding hardware. So the risk of contaminant infiltration back through the window opening will vary depending on the actual component arrangement and relative structural configuration of system components in a given embodiment and application.

To the extent needed, therefore, this exposed portion of the window opening is preferably protected about the hook and hook holding hardware to shield against contaminant infiltration. For example, the surrounding window opening space is shielded by a cover shaped and sized to be almost as big or as big as the window opening itself. In other words, the shield would extend transversely about the hook/hook holding hardware at or near the base of the hooks (proximate end of the hook away from the distal tips thereof) to block the opening thereabout.

Preferably, such shield may actually be placed in front of the window opening's slot, so that the base of the hook could almost completely cover the slot. The slot is preferably elongated. And then the part of each hook that's actually engaged in the slot—to be laterally displaced therein—is not that wide. However, there is a front shield on each hook that spreads to cover the open spaces thereabout. They're like wings on either side so that when these two wings are spread—when the two hooks are in the middle joined together—then, the wings are wide enough to cover the outer parts of the slot. And then inside the slot when the hooks are slid over it, the wings would likewise move over. To cover the space between the two hooks, an overlapping attachment region or other suitable measure known in the art may be employed to provide shielding coverage over most if not all of the space laterally between the hooks.

Preferably, a cover used for shielding the window opening falls away with the used hooks to preserve a clean barrier against contaminant infiltration. A simpler structure might employ a flexible, reusable barrier with perhaps slits or other accommodating measures formed therein (through which the hooks may push out through—much like a curtain). While sufficient going one way because the hooks extending out each time are new, once the hooks are used, there is contamination of the hook holding hardware that retracts for loading with the next set of hooks to be used. Although the used hooks may have been released and discarded, there remains the risk of the holding hardware's residual contamination, which would follow the hardware's retraction back into the clean storage compartment for new hooks. Aside from this risk, even if the holding hardware were retracted without residual contamination, any newly-loaded hook passing out through the curtain-like barrier may suffer contamination from material remaining on the barrier's outer surface (that has already been exposed to the contaminant during previous de-gloving action) as the hook pushes outward therethrough into its initial de-gloving position.

As mentioned already, another way of introducing the hooks is to enter from the top, making a 180-degree arcing motion. That may be preferable in some instances because that option eliminates any exposed slot at the active de-gloving area's level. In that case, the hooks would drop in from the top.

Preferably, many if not all of the automated movements are electromechanically driven. Other suitable forms of automated actuation known in the art may be employed for a given embodiment and application.

Regarding what triggers the separation between the glove and hand, as described in preceding paragraphs, a puff of air is preferably blown therebetween to urge or assist this separation. When employed, such puff of air maybe variously triggered by any suitable means known in the art, such as by manually initiated switching, by timing or pressure sensor-responsive automatic switching, or the like. Like or similar measures may be used to trigger another separation, namely the lateral separating movement between hook members once they've engaged the glove, to gently expand the opening for effortless withdrawal of the hand.

For example, when the user pulls the hand, he/she applies a vertical load to the hook and that may trigger the lateral separation. This would be in contrast to perhaps the simplest implementation case, where the hooks were simply actuated to come out and let the user grab hold of it by manipulating their hands and then just manually work the hands to move them out of the held gloves gently and slowly. That may work if necessary, but the degree of effectiveness will vary depending on the particular factors involved in a given application, factors like the elasticity of the glove material, and the like. Experimentation with typical surgical gloves indicates that it may be easier and more safely practicable to withdraw the hand after lateral mutual separation of engaging hooks to part/expand the opening for hand removal.

Figure 16:
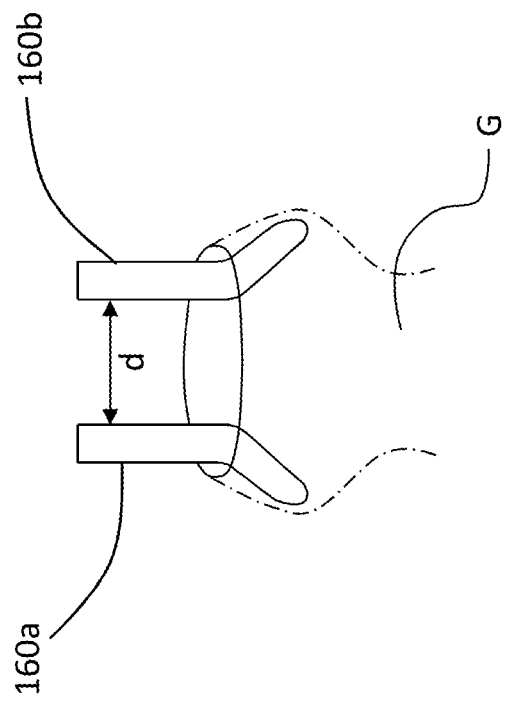
FIG. 16 is a schematic diagram illustratively showing a pair of hook members disposed in mutually spaced and stationary manner in a system realized in accordance with another alternate embodiment of the present invention, where each hook member remains stationary during de-gloving engagement of a glove worn on a user's hand; and, FIGS. 17-A and 17-B are schematic diagrams illustratively showing examples of complementarily shaped hook member configurations which may be cooperatively employed in a system realized in accordance with another alternate embodiment of the present invention, where each hook member remains stationary during de-gloving engagement of a glove worn on a user's hand.
Figure 15:
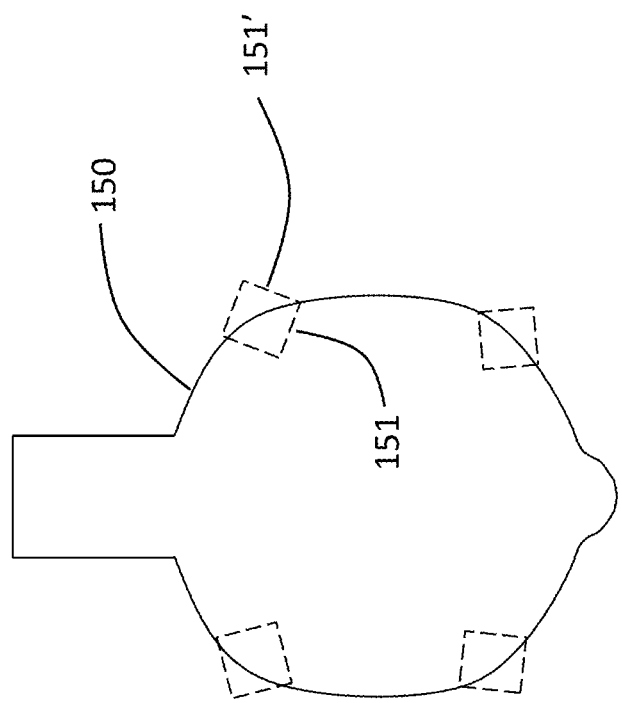
FIG. 15 is a schematic diagram illustratively showing one example of a hook member configuration which may be employed in a system realized in accordance with yet another alternate embodiment of the present invention, where each hook member remains stationary during de-gloving engagement of a glove worn on a user's hand.

Simpler cases may make use of one or more hooks which remain stationary once the glove material is engaged to begin de-gloving, as opposed to using hooks a separator mechanism which draws them apart to widen the mouth of the glove once the glove material is engaged. For example, just one disposable hook may be introduced and positioned for the user so that he/she may then manipulate the glove on a hand into engagement with the hook, then works the hand out of the glove. The hook need not be formed as just a plain thin piece. It may be variously shaped to suit the requirements of the particularly intended application. It may be shaped for instance wider at certain portions like a shoehorn of sorts, so as to optimize and facilitate grip of the glove from the user's gloved hand. Illustrative examples are shown in FIGS. 15-16, 17-A, and 17-B.

In such simpler cases, the force required to guide and supportingly position a single hook as opposed to multiple separate hooks would be less. Consequently, there's less total force and energy required of the system to remove the glove. But the wider part of the hand—where the opening of the glove normally conforms to for retention, will tend to resist removal of the glove.

Although it may require more complex, delicate, and trickier mechanical movement, in certain embodiments, one or more of the hooks may extend out with multi-dimensional movement. For example, the hooks may not only projecting out from the back wall of the housing (in the illustrated embodiment), but also by angularly rotating at the appropriate time so that the shape of the hook along a given plane changes. If the change in span of an engaging portion of the hook were great enough, the rotational displacement (or reorientation) of the hook would serve as a separating guide. Once the hook inserts deeply enough in between the glove and hand, and then turns, the turning of it would urge the glove material away from the skin.

Such turning of the hook raises some complications. For example, when the user is trying to remove the glove, and if the hook is completely vertical, there is the possibility of having the glove somewhat coming off the hook. But if the hook were far enough away from vertical, or 90 degrees, disposed for instance at 110 degrees angle or orientation, it would provide a claw-like configuration. But when the hook is turned, it could actually rip the glove if not carefully done, or if not suitably shaped. But the glove would not readily release from the hook because of the hook's would stretching engagement towards the back. The hook would typically not simply extend straight down the glove's rubber surface if there's even a slight intermediate bend. Enough tension would result in the hook's engagement with the glove that the glove will tend not to simply slide off.

Also, the glove will not tend to slide off too easily if it is formed of latex-type glove material, due to inherent friction/adhesion properties. Even if the glove (and hand) were disposed at approximately 90 degrees, it normally would not release from the hook because at some point it will be sufficiently tensioned to the hook to yield enough frictional adhesion.

Still, it is preferable for the hook to be shaped to enhance grip of the glove material. For example, the hook may be formed with an overall shape that slants outward. Opposed hook members would then cooperatively form a generally pigeon toed configuration. By way of another example, the hook members may cooperatively form a scissor-like coupling and configuration.

If just one hook member is used for glove engagement, suitable measures may be employed as necessary to provide a scissor-like expanding mechanism at or near its tip. This would be implemented as needed to widen with whatever angulation and degree may be required for a given application. The disadvantage of this would be the added cost and complexity of incorporating moving parts at the end of the hook.

An example of another variation is multiple hook formations emerging from a common base. So instead of multiple separately-structured hooks, one hook member would provide multiple hook formations spread apart in a widened configuration. For example, a double-pronged hook that attaches so that there are no slits needed at the back wall of the box system housing.

In yet another alternate configuration, two hooks start out separated but they're disposed in a pigeon-toed arrangement. For instance, they may bend downwards such that the two bent portions form substantially a V shape, much like a wedge. Then if a user draws their hand between the glove-engaging hooks, instead of the hooks simply inserting deeper into the glove, their wedge formation would simultaneously urge the glove away from and off the hand. Such pigeon-toed combination of hooks would serve to decrease the user effort required for glove removal.

With such V shaped hook formation, as the gloved hand is moved up the hook, de-gloving may be naturally urged without movement of the hooks themselves. But the frictional contact between the glove material and hooks may be prohibitive with certain glove materials like latex and the like, unless suitable remedial measures are taken.

Regarding the double prong hook options, a consideration is that it creates two points of entry into the glove. A more practicable option may be for the hooks to be disposed that they enter the glove at a single or combined point, with the hooks then opening up (such as by working them apart from one another), to essentially form an A shaped movement. But if the hooks do not remain parallel, a potential risk results when a user tries to pull the hand out, the hooks insert deeper into the glove, potentially snagging, puncturing, and tearing the glove.

So the hooks are preferably formed with gently rounded tips and edges, to minimize this risk of snagging and tearing the glove material. It is preferable thereby to form the hooks to insert deep into the glove, gliding as much as possible between the glove material and skin, so that the whole process remains very smooth.

The last thing that one would want to do as one tries to remove the glove is to cause the glove to snag, catch, and abruptly release to sling-shot project the contaminant material in random directions. Ideally, the inside out removal would start at the base of the hand to the tip of the finger, with the removal progressing gradually and smoothly. If there is a snagging catch of the glove material, and removal starts from a more intermediate point, then things may get messy, increasing the risk of unwanted splatter.

So it's preferable to somewhat uniformly stretch the glove's opening, enabling the user to then neatly pull the hand out. Typically, if the user tries to open the glove with one hook without expanding the opening, the glove tends to stick. Excess force concentration in certain spots occur, causing uneven stretching of the glove material, and leading to unpredictable tensioning and release of material which again raises the risk of unwanted, potentially hazardous contaminant projection, especially with perspiration and condensation inside the glove making for random slippage conditions.

Preferably, getting two finger-like hooks inserted into the glove's opening provides even, balanced engagement and opening of the glove. The even and balanced stretching preserves stability and squares the opening for smooth hand removal and inside-out withdrawal of the glove's extremities.

Analogously, this emulates a human assistant using two hands to de-glove an individual's gloved hand, or the combined efforts of two assistants. When an assistant tries to de-glove using but one hand, they risk distorted, unbalanced stretching of the glove and consequent splattering of both themselves, the glove wearer, and whomever else or whatever else may be in the room—if not an individual, then perhaps a seat. The threat of aerosolized virus contaminating chairs, walls, and articles which individuals later touch or carry is thereby enhanced.

Even if gloves are carefully used, noxious materials and agents—whether it's bacteria that travel through saliva or blood, or something else—transmission occurs despite such precautions because there's a breach in some barrier at a certain point, leading to contamination through the mouth, respiratory tract, or through direct blood-blood contact.

In many applications, especially in the context of healthcare, it is critical to preserve the sanitary integrity of the system. So the system housing preferably has internal walls which are suitably lined or otherwise protected via disposable membranous measures at the most vulnerable portions. Examples include lining inner surfaces with a plastic cover or other removable, replaceable barrier. Where a flexible plastic liner is employed, hooks, adhesives, or other such suitable fastening measures may be employed as needed to retain the liner in place during operation. Preferably, the liner is formed much like a flexible garbage bag or trash bin liner formed of biodegradable material.

Preferably, such liner extends fully up to the base of the hook admitting slot (which is preferably gated shut, except for de-gloving operation). Other variations of such liner may be employed. The liner that may be changed once a day, every couple hours, or at any other required interval, depending on how frequently de-gloving is carried out. Trial and error experimentation may be conducted to determine the ideal and necessary portions of the housing's inner wall surfaces to be lined or otherwise protected, once an operation system/device is implemented. For example, one may cover a glove with trackable material, such as some radioactive or electroluminescent material, and see where the material ends up after different trial de-gloving operations. So it's testable, and the protection effectively tunable to a certain measurable amount/degree of protective barrier preservation.

Another possible variation is to form a manual version of the system. The movements of such embodiment and application would be mechanically driven, albeit manually actuated. The movements may even be manually controlled by an assistant outside the housing, for instance, behind the ample safety of a protective shield of barrier.

So depending on the level of automation is desired, or needed—where one is working in an HIV clinic, for instance, a high degree of automation may be desired to minimize undue risk of exposing others—the system may be suitably implemented accordingly. Where the strictest barrier against contaminant transmission is to be preserved, a plethora of disposable elements that may be employed—from different housing components to various separate protective liners and the like—to ensure that every single thing inside goes to trash, even the liners, with but one time use. Multiple uses may be more conceivable outside hospital settings, such as for instance in a workplace setting like a restaurant where the threat to health is less critical. The more modest requirements for disposable elements typically require less expensive system implementations.

Turning to the hook feeding assembly and mechanism, in the simplest form an attendant may supply the needed hooks from an external booth through a hook admission slot, and manually supplying a new set of hooks as they are used and disposed of. At a basic level of implementation, the attendant could just put a new set of prongs and hooks in through the admission, then operate a separation mechanism so that at the glove wearer's prompt, the attendant actuates the separator mechanism to move the hooks apart. Use of mechanically automated or powered mechanisms may be preferable but not necessary in such implementations. As described in preceding paragraphs, the more automated implementations would add such features as a motion sensor for automatic actuation, as well as other features.

Turning to the material compositions of various system components, any suitable materials known in the art may be used. Depending on the particularly intended application, the combination of cost, strength, rigidity, and resistance to contaminants would be amongst the more determinative factors. Each of the hooks may be formed of such materials as plastic or any other material that is inexpensive, strong, and rigid enough to provide the needed support throughout a de-gloving process. The system's housing may be formed, for example, of such materials as metal, plastic, wood, glass, or combinations thereof to realize a strong, stable, yet easily handled and maintainable yet structurally sound construction.

In certain applications, the system may be free standing. In others it may be mounted to the floor or wall structure, even hanging on a wall suspended from the floor, where available square footage may be scarce. This may be the case, particularly, in hospital setting settings where the available space for such de-gloving system may often be within a small preparatory room or within a very limited area of an operating room.

For example, the system may be disposed at or near the sink area where care givers scrub their arms and hands. There would be a sink station, where one washes one's hands, then a gloving station where one puts on the gloves. Then after performing the given procedure, the user heads to the nearby de-gloving station that may be situated next to the trash/waste station. The user then comes out of the de-gloving station, and returns to the sink station to wash their hands again before departing.

In lieu or a wall mount implementation, the system may be configured for mounting to a desk, table, cabinet, or other such item, console, fixture, or other such structure having an access opening or compartment underneath for direct discarding and safe containment of spent gloves and the contaminants they carry.

The supporting structure may be suitably coupled to a chute which may directly conduct the discarded waste directly into a waste management system/facility.

To clean the system, the user in most applications need only open the lid/cover with the hook admitting mechanism disabled, then simply remove the filled wasted bag. The bag may then be wrapped up and dumped it into a place where they dispose biodegradable material. This may be done once a day or more/less frequently depending on how dirty the transmittable material is. If any stray material remains within the system's housing due to splattering during use, regular cleaning and sterilization procedure should normally prevent the risk from residual effects.

The system is preferably cleaned thoroughly this way. The required regular cleaning poses far less risk to support staff than having to help remove contaminated gloves and the potential for exposure to active contaminants, infectious agents, or the like.

Referring back to the system embodiment shown in FIGS. 11-14, the mechanical box 9' preferably contains a chamber or cartridge of disposable hooks. Once a hook is used up, another gets pushed out. If two or more hooks are cooperatively used during de-gloving, respective supply cartridges or compartments are established in this regard to supply each of the cooperating hooks. Preferably, one or more motor-driven mechanisms are suitably formed and disposed to push the hooks out and thereafter move them as needed to support the de-gloving operation.

Preferably, the system's components are highly modular in construction, so that system is easily cleaned and maintained. If one needs to clean an empty mechanical box, for instance, one can clean it without having to worry about the electronics. By way of example, the electronic mechanical box compartment 9' may be modular to the extent that it would be replaceable as a module unto itself. So it may be configured much like a mechanical cartridge that may be inserted into an accommodating receptacle, suitably attached and releasably fastened for use. When ready to be cleaned or after sufficient service life, it may be readily removed for cleaning, servicing, or replacement.

Although this invention has been described in connection with specific forms and embodiments thereof, it will be appreciated that various modifications other than those discussed above may be resorted to without departing from the spirit or scope of the invention as defined herein. For example, functionally equivalent elements or processes may be substituted for those specifically shown and described, certain features may be used independently of other features, and in certain cases, and particular locations of the elements or processes may be reversed or interposed, all without departing from the spirit or scope of the invention as defined herein.

What is claimed is:

1. A system for safe removal and disposal of a glove from a user's hand, comprising:
    a mainframe defining a de-gloving compartment;
    at least one hook base portion displaceably supported relative to said mainframe; and,
    at least one hook member coupled to said hook base portion, at least a part of said hook member defining a disposable portion detachable from said hook base portion, said disposable portion of said hook member terminating at an engaging tip configured for insert within the glove worn on the user's hand;
    said hook base portion being displaceable to selectively position said engaging tip of said hook member into said de-gloving compartment, the glove being removed responsive to relative displacement between said engaging tip and the user's hand upon engagement of the glove worn thereon;
    wherein the removed glove is released with said disposable portion upon detachment thereof from said hook base portion into a receptacle disposed in communication with said de-gloving compartment, said hook base portion remaining shielded from said de-gloving compartment.

2. The system as recited in claim 1, further comprising a hands-free control portion coupled to actuate the displacement of said hook base portion and release of said disposable portion of said hook member therefrom responsive to a predetermined user prompt.

3. The system as recited in claim 2, wherein said disposable portion of said hook member is matingly coupled in releasably locked manner to said hook base portion.

4. The system as recited in claim 3, wherein said hook base portion includes at least one tab retractably extending therefrom to retentively engage said disposable portion of said hook member.

5. The system as recited in claim 1, further comprising a blower mechanism coupled to said hook base portion, said blower mechanism being pneumatically coupled to said hook member to selectively actuate a flow of air through the engaging tip thereof for separating the glove from a surface of the user's hand.

6. The system as recited in claim 1, wherein said hook base portion is coupled to said mainframe by a main mechanism, said main mechanism being displaceable relative to said mainframe along at least a first dimensional reference, said hook base portion being displaceable relative to said main mechanism along at least a second dimensional reference responsive to user actuation of a hands-free control portion.

7. The system as recited in claim 1, wherein said hook base portion includes at least first and second components having first and second hook members respectively coupled thereto for cooperatively engaging the same glove on a user's hand, said first and second components of said hook base portion being mutually displaceable for widening an opening of the glove about the user's hand.

8. The system as recited in claim 1, further comprising a splash guard portion projecting from said mainframe to partition said hook base portion from said de-gloving zone therebeneath, said hook member extending from said hook base portion to reach around and beyond a terminal edge of said splash guard portion to suspend said engaging tip within said de-gloving zone.

9. The system as recited in claim 1, further comprising at least one dispensing cartridge coupled to said mainframe, said dispensing cartridge storing a plurality of replacements for said disposable portion of said hook member, said hook base portion being selectively displaceable relative to dispensing cartridge to receive a replacement of said disposable portion therefrom.

10. A method for safe removal and disposal of a glove from a user's hand, comprising:
    establishing a mainframe and defining a de-gloving compartment therein;
    displaceably supporting at least one hook base portion relative to said mainframe;
    displaceably carrying at least one hook member on said hook base portion, with at least a part of said hook member defining a disposable portion detachable from said hook base portion;
    terminating said disposable portion of said hook member at an engaging tip configured for insert within the glove worn on the user's hand;
    displacing said hook base portion to selectively position said engaging tip of said hook member into said de-gloving compartment;
    removing the glove with said disposable portion of said hook member responsive to relative displacement between said engaging tip and the user's hand upon engagement of the glove worn thereon; and,
    maintaining said hook base portion shielded from said de-gloving compartment;
    whereby the removed glove is safely released with said disposable portion upon detachment thereof from said hook base portion into a receptacle disposed in communication with said de-gloving compartment.

11. The method as recited in claim 10, further comprising actuating a hands-free control portion to displace said hook base portion and release of said disposable portion of said hook member therefrom responsive to a predetermined user prompt.

12. The method as recited in claim 10, further comprising pneumatically actuating a puff of air through the engaging tip of said hook member to separate the glove from a surface of the user's hand.

13. The method as recited in claim 10, wherein said hook base portion is coupled to said mainframe by a main mechanism, said main mechanism is displaceable relative to said mainframe along at least a first dimensional reference, and said hook base portion is displaceable relative to said main mechanism along at least a second dimensional reference responsive to user actuation of a hands-free control portion.

14. The method as recited in claim 1, wherein at least first and second components are established in each said hook base portion for respectively carrying first and second hook members for cooperatively engaging the same glove on a user's hand, mutually displacing said first and second components of said hook base portion for widening an opening of the glove about the user's hand.

15. The method as recited in claim 10, further comprising establishing a splash guard portion projecting from said mainframe to partition said hook base portion from said de-gloving zone therebeneath, configuring said hook member to extending from said hook base portion to reach around and beyond a terminal edge of said splash guard portion and thereby suspend said engaging tip within said de-gloving zone.

* * * * *